US012806420B2

(12) United States Patent
Wang et al.

(10) Patent No.: US 12,806,420 B2
(45) Date of Patent: Nov. 24, 2026

(54) SYSTEM AND METHOD FOR DEEP BRAIN STIMULATION

(71) Applicant: THE BOARD OF REGENTS OF THE UNIVERSITY OF TEXAS SYSTEM, Austin, TX (US)

(72) Inventors: Xiaoliang Wang, Dallas, TX (US); Bradley Lega, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 274 days.

(21) Appl. No.: 18/502,619

(22) Filed: Nov. 6, 2023

(65) Prior Publication Data

US 2024/0157149 A1 May 16, 2024

Related U.S. Application Data

(60) Provisional application No. 63/383,127, filed on Nov. 10, 2022.

(51) Int. Cl.

| | |
|---|---|
| ***A61N 1/36*** | (2006.01) |
| ***A61N 1/02*** | (2006.01) |
| ***A61N 1/05*** | (2006.01) |
| ***G16H 20/30*** | (2018.01) |

(52) U.S. Cl.

CPC ......... *A61N 1/36135* (2013.01); *A61N 1/025* (2013.01); *A61N 1/0534* (2013.01); *G16H 20/30* (2018.01)

(58) Field of Classification Search

CPC .................. A61N 1/025; A61N 1/0534; A61N 1/36135; A61N 1/36139; G16H 20/30

See application file for complete search history.

(56) References Cited

U.S. PATENT DOCUMENTS

| | | | |
|---|---|---|---|
| 7,974,696 | B1 | 7/2011 | DiLorenzo |
| 9,173,609 | B2 | 11/2015 | Nelson |
| 9,566,426 | B2 | 2/2017 | Simon et al. |
| 10,265,497 | B2 | 4/2019 | Tsai et al. |
| 10,478,639 | B2 | 11/2019 | Lee et al. |

(Continued)

FOREIGN PATENT DOCUMENTS

WO WO-2022094123 A1 * 5/2022 ............. A61N 2/006

OTHER PUBLICATIONS

Jeong, J. (2004). "EEG dynamics in patients with Alzheimer's disease". In: Clinical neurophysiology 115.7, pp. 1490-1505.

(Continued)

*Primary Examiner* — Amanda K Hulbert
(74) *Attorney, Agent, or Firm* — Polsinelli PC

(57) ABSTRACT

A cystoscopy system with intracranial electrodes operable to be disposed in a hippocampus region of a brain and configured to record electrical signals that include biomarkers related to memory encoding, a neurostimulator configured to stimulate a posterior cingulate cortex (PCC) of the brain, a NARXNN plant model, and a controller configured to receive the electrical signals and modulate an input/output (I/O) relationship between the biomarkers and electrical stimuli applied to a posterior cingulate cortex (PCC) of the brain by controlling the neurostimulator to stimulate the PCC based on the I/O relationship to achieve a desired level of the biomarkers.

17 Claims, 13 Drawing Sheets

(56) References Cited

U.S. PATENT DOCUMENTS

| | | | | |
|---|---|---|---|---|
| 10,512,769 | B2 | 12/2019 | Simon et al. | |
| 10,898,706 | B2 | 1/2021 | Pradeep | |
| 2020/0139113 | A1 | 5/2020 | Shin et al. | |
| 2022/0240846 | A1 | 8/2022 | Howard | |
| 2024/0017069 | A1 * | 1/2024 | Widge | A61N 1/36082 |

OTHER PUBLICATIONS

Jones, M.W. et al. (2005). “Phase precession of medial prefrontal cortical activity relative to the hippocampal theta rhythm”. In: Hippocampus 15.7, pp. 867-873.
Kailath, T. (1998). Linear Systems. Prentice-Hall information and system sciences series. Prentice Hall International.
Kannathal, N. et al. (2005). “Characterization of EEG—a comparative study”. In: Computer methods and Programs in Biomedicine 80.1, pp. 17-23.
Kay, S.M. (1988). Modern Spectral Estimation. Prentice Hall.
Kerr, K. M. et al. (2007). “Functional neuroanatomy of the parahippocampal region: the lateral and medial entorhinal areas”. In: Hippocampus 17.9, pp. 697-708.
Khalsa, S. et al. (2014). “The structural and functional connectivity of the posterior cingulate cortex: Comparison between deterministic and probabilistic tractography for the investigation of structure-function relationships”. In: Neuroimage 102, pp. 118-127.
Klimesch, W. (1999). “EEG alpha and theta oscillations reflect cognitive and memory performance: a review and analysis”. In: Brain research reviews 29.2-3, pp. 169-195.
Knierim, J. J. (2015). “The hippocampus”. In: Current Biology 25.23, R1116-R1121.
Kota, S., M. D. Rugg, and B. C. Lega (2020). “Hippocampal theta oscillations support successful associative memory formation”. In: Journal of Neuroscience 40.49, pp. 9507-9518.
Kringelbach, M. L. et al. (2007). “Translational principles of deep brain stimulation”. In: Nature Reviews Neuroscience 8.8, pp. 623-635.
Kucewicz, M.T. et al. (2018). “Evidence for verbal memory enhancement with electrical brain stimulation in the lateral temporal cortex”. In: Brain 141.4, pp. 971-978.
Lachaux, J.-P. et al. (1999). “Measuring phase synchrony in brain signals”. In: Human brain mapping 8.4, pp. 194-208.
Lakatos, P. et al. (2005). “An oscillatory hierarchy controlling neuronal excitability and stimulus processing in the auditory cortex”. In: Journal of neurophysiology 94.3, pp. 1904-1911.
Lamus, C. et al. (2012). “A spatiotemporal dynamic distributed solution to the MEG inverse problem”. In: NeuroImage 63.2, pp. 894-909.
Laxton, A.W. et al. (2013). “Deep brain stimulation for the treatment of Alzheimer disease and dementias”. In: World neurosurgery 80.3-4, S28-e1.
Lega, B. et al. (2014). “Slow-theta-to-gamma phase-amplitude coupling in human hippocampus supports the formation of new episodic memories”. In: Cerebral Cortex 26.1, pp. 268-278.
Lega, B. et al. (2017). “Modulation of oscillatory power and connectivity in the human posterior cingulate cortex supports the encoding and retrieval of episodic memories”. In: Journal of cognitive neuroscience 29.8, pp. 1415-1432.
Lega, B.C. et al. (2010). “Deep brain stimulation in the treatment of refractory epilepsy: update on current data and future directions”. In: Neurobiology of disease 38.3, pp. 354-360.
Lega, B.C. et al. (2011). “Neuronal and oscillatory activity during reward processing in the human ventral striatum”. In: Neuroreport 22.16, p. 795.
Leontaritis, I. et al. (1985). “Input-output parametric models for non-linear systems part I: deterministic non-linear systems”. In: International journal of control 41.2, pp. 303-328.
Lilly, J.M. et al. (2012). “Generalized Morse wavelets as a superfamily of analytic wavelets”. In: IEEE Transactions on Signal Processing 60.11, pp. 6036-6041.
Lin, J.-J. et al. (2017). “Theta band power increases in the posterior hippocampus predict successful episodic memory encoding in humans”. In: Hippocampus 27.10, pp. 1040-1053.
Lin, J.-J. et al. (2019). “Gamma oscillations during episodic memory processing provide evidence for functional specialization in the longitudinal axis of the human hippocampus”. In: Hippocampus 29.2, pp. 68-72.
Lisman, J.E. et al. (2013). “The theta-gamma neural code”. In: Neuron 77.6, pp. 1002-1016.
Ljung, L. (2020). System Identification Toolbox User’s Guide. MathWorks.
Ljung, L. (1999). System Identification (2nd Ed.): Theory for the User. USA: Prentice Hall PTR.
Ljung, L. (2007). Practical issues of system identification. Link oping University Electronic Press. Lozano, A. M. et al. (2016). “A phase II study of fornix deep brain stimulation in mild Alzheimer’s disease”. In: Journal of Alzheimer’s Disease 54.2, pp. 777-787.
Lozano, A.M., et al. (2016). “A Phase II Study of Fornix Deep Brain Stimulation in Mild Alzheimer’s Disease,” Journal of Alzheimer’s Disease, vol. 54, p. 777-787.
Lozano-Soldevilla, D. et al. (2016). “Neuronal oscillations with non-sinusoidal morphology produce spurious phase-to-amplitude coupling and directionality”. In: Frontiers in computational neuroscience 10, p. 87.
Maass, A. et al. (2015). “Functional subregions of the human entorhinal cortex”. In: Elife 4, e06426.
Macdonald, D.B. (2002). “Safety of intraoperative transcranial electrical stimulation motor evoked potential monitoring”. In: Journal of clinical neurophysiology 19.5, pp. 416-429.
Mackay, D.J. (1992). “Bayesian interpolation”. In: Neural computation 4.3, pp. 415-447.
Malone Jr, D. A. et al. (2009). “Deep brain stimulation of the ventral capsule/ventral striatum for treatment-resistant depression”. In: Biological psychiatry 65.4, pp. 267-275.
Mankin, E.A et al. (2020). “Modulation of Human Memory by Deep Brain Stimulation of the Entorhinal-Hippocampal Circuitry”. In: Neuron 106.2, pp. 218-235.
Manning, J.R. et al. (2011). “Oscillatory patterns in temporal lobe reveal context reinstatement during memory search”. In: Proceedings of the National Academy of Sciences 108.31, pp. 12893-12897.
Manns, J.R. et al. (2007). “Hippocampal CA1 spiking during encoding and retrieval: relation to theta phase”. In: Neurobiology of learning and memory 87.1, pp. 9-20.
Marinescu, R. et al. (2019). “BrainPainter: A software for the visualisation of brain structures, biomarkers and associated pathological processes”. In: arXiv preprint arXiv:1905.08627.
Mayberg, H.S. et al. (2005). “Deep brain stimulation for treatment-resistant depression”. In: Neuron 45.5, pp. 651-660.
McNaughton, N. et al. (2006). “Restoring theta-like rhythmicity in rats restores initial learning in the Morris water maze”. In: Hippocampus 16.12, pp. 1102-1110.
Menezes Jr, J. M.P. et al. (2008). “Long-term time series prediction with the NARX network: An empirical evaluation”. In: Neurocomputing 71.16-18, pp. 3335-3343.
Miao, B. et al. (2005). “System identification of power converters with digital control through cross-correlation methods”. In: IEEE Transactions on Power Electronics 20.5, pp. 1093-1099.
Miller, J. et al. (2018). “Lateralized hippocampal oscillations underlie distinct aspects of human spatial memory and navigation”. In: Nature communications 9.1, pp. 1-12.
Miranda, R.A. et al. (2015). “DARPA-funded e• orts in the development of novel brain-computer interface technologies”. In: Journal of neuroscience methods 244, pp. 52-67.
Møller, A.R. (1986). “Systems identification using pseudorandom noise applied to a sensorineural system”. In: Computers & Mathematics with Applications 12.6, pp. 803-814.
Monmasson, E. et al. (2011). “FPGAs in industrial control applications”. In: IEEE Transactions on Industrial informatics 7.2, pp. 224-243.
Mormann, F. et al. (2005). “Phase/amplitude reset and theta-gamma interaction in the human medial temporal lobe during a continuous word recognition memory task”. In: Hippocampus 15.7, pp. 890-900.

(56) References Cited

OTHER PUBLICATIONS

Musk, E. et al. (2019). "An integrated brain-machine interface platform with thousands of channels". In: Journal of medical Internet research 21.10, e16194.
Natu, V.S. et al. (2019). "Stimulation of the posterior cingulate cortex impairs episodic memory encoding". In: Journal of Neuroscience 39.36, pp. 7173-7182.
Negron-Oyarzo, I. et al. (2018). "Coordinated prefrontal-hippocampal activity and navigation strategy-related prefrontal firing during spatial memory formation". In: Proceedings of the National Academy of Sciences 115.27, pp. 7123-7128.
Agarwal, G. et al. (2014). "Spatially distributed local fields in the hippocampus encode rat position". In: Science 344.6184, pp. 626-630.
Agnew, W.F. et al. (1990). "Considerations for safety with chronically implanted nerve electrodes". In: Epilepsia 31, S27-S32.
Anderson, R. et al. (2020). "A novel method for calculating beta band burst durations in Parkinson's disease using a physiological baseline". In: Journal of neuroscience methods 343, p. 108811.
Ardalani-Farsa, M. et al. (2010). "Chaotic time series prediction with residual analysis method using hybrid Elman-NARX neural networks". In: Neurocomputing 73.13-15, pp. 2540-2553.
Arora, A. et al. (2018). "Comparison of logistic regression, support vector machines, and deep learning classifiers for predicting memory encoding success using human intracranial EEG recordings". In: Journal of neural engineering 15.6, p. 066028.
Aru, J. et al. (2015). "Untangling cross-frequency coupling in neuroscience". In: Current opinion in neurobiology 31, pp. 51-61.
Astrom, K.J., et al. (2006). Advanced PID control. vol. 461. ISA—The Instrumentation, Systems, and Automation Society Research Triangle Park.
Axmacher, N. et al. (2010). "Cross-frequency coupling supports multi-item working memory in the human hippocampus". In: Proceedings of the National Academy of Sciences 107.7, pp. 3228-3233.
Backman, L., et al. (2001). "Stability of the preclinical episodic memory deficit in Alzheimer's disease". In: Brain 124.1, pp. 96-102.
Backus, A.R et al. (2016). "Hippocampal-prefrontal theta oscillations support memory integration". In: Current Biology 26.4, pp. 450-457.
Baddeley, A.D. et al. (1970). "Amnesia and the distinction between long-and short-term memory". In: Journal of verbal learning and verbal behavior 9.2, pp. 176-189.
Bai, F. et al. (2009). "Abnormal resting-state functional connectivity of posterior cingulate cortex in amnestic type mild cognitive impairment". In: Brain research 1302, pp. 167-174.
Basu, I. et al. (2018). "A neural mass model to predict electrical stimulation evoked responses in human and non-human primate brain". In: Journal of neural engineering 15.6, p. 066012.
Basu, J. et al. (2015). "The corticohippocampal circuit, synaptic plasticity, and memory". In: Cold Spring Harbor perspectives in biology 7.11, a021733.
Benabid, A.L. (2003). "Deep brain stimulation for Parkinson's disease". In: Current opinion in neurobiology 13.6, pp. 696-706.
Blanco, S. et al. (1995). "Stationarity of the EEG series". In: IEEE Engineering in medicine and biology Magazine 14.4, pp. 395-399.
Bouthour, W. et al. (2019). "Biomarkers for closed-loop deep brain stimulation in Parkinson disease and beyond". In: Nature Reviews Neurology 15.6, pp. 343-352.
Breit, S., J. B. Schulz, and A.-L. Benabid (2004). "Deep brain stimulation". In: Cell and tissue research 318.1, pp. 275-288.
Bressler, S. L., R. Coppola, and R. Nakamura (1993). "Episodic multiregional cortical coherence at multiple frequencies during visual task performance". In: Nature 366.6451, pp. 153-156.
Bullock, T.H. et al. (1989). "Lateral coherence of the electrocorticogram: a new measure of brain synchrony". In: How do Brains Work? Springer, pp. 375-396.
Burgess, N., et al. (2002). "The human hippocampus and spatial and episodic memory". In: Neuron 35.4, pp. 625-641.
Burke, J. F. et al. (2014). "Theta and high-frequency activity mark spontaneous recall of episodic memories". In: Journal of Neuroscience 34.34, pp. 11355-11365.
Buschman, T. J. et al. (2012). "Synchronous oscillatory neural ensembles for rules in the prefrontal cortex". In: Neuron 76.4, pp. 838-846.
Butson, C. R. et al. (2007). "Patient-specific analysis of the volume of tissue activated during deep brain stimulation". In: Neuroimage 34.2, pp. 661-670.
Buzsaki, G. (2002). "Theta oscillations in the hippocampus". In: Neuron 33.3, pp. 325-340.
Cabeza, R. et al. (2008). "The parietal cortex and episodic memory: an attentional account". In: Nature Reviews Neuroscience 9.8, pp. 613-625.
Canolty, R.T. et al. (2006). "High gamma power is phase-locked to theta oscillations in human neocortex". In: science 313.5793, pp. 1626-1628.
Canolty, R.T. et al. (2010). "The functional role of cross-frequency coupling". In: Trends in cognitive sciences 14.11, pp. 506-515.
Canto, C. B., F. G. Wouterlood, and M. P. Witter (2008). "What does anatomical organization of entorhinal cortex tell us?" In: Neural plasticity.
Chaieb, L. et al. (2015). "Theta-gamma phase-phase coupling during working memory maintenance in the human hippocampus". In: Cognitive neuroscience 6.4, pp. 149-157.
Chang, J.-Y. et al. (2012). "Multivariate autoregressive models with exogenous inputs for intracerebral responses to direct electrical stimulation of the human brain". In: Frontiers in human neuroscience 6, p. 317.
Choi, K. et al. (2020). "Longitudinal di• erences in human hippocampal connectivity during episodic memory processing". In: Cerebral cortex communications 1.1, tgaa010.
Coffey, R.J. (2009). "Deep brain stimulation devices: a brief technical history and review". In: Artificial organs 33.3, pp. 208-220.
Cole, S. et al. (2019). "Cycle-by-cycle analysis of neural oscillations". In: Journal of neurophysiology 122.2, pp. 849-861.
Colgin, L.L. (2015). "Theta-gamma coupling in the entorhinal-hippocampal system". In: Current opinion in neurobiology 31, pp. 45-50.
Colgin, L.L. et al. (2009). "Frequency of gamma oscillations routes flow of information in the hippocampus". In: Nature 462.7271, pp. 353-357.
Coombes, S. et al. (2019). "Next generation neural mass models". In: Nonlinear dynamics in computational neuroscience. Springer, pp. 1-16.
Corripio, I. et al. (2020). "Deep brain stimulation in treatment resistant schizophrenia: a pilot randomized cross-over clinical trial". In: EBioMedicine 51, p. 102568.
Dan, Y. et al. (2006). "Spike timing-dependent plasticity: from synapse to perception". In: Physiological reviews 86.3, pp. 1033-1048.
Daunizeau, J. et al. (2007). "A mesostate-space model for EEG and MEG". In: NeuroImage 38.1, pp. 67-81.
Davila, C.E. (2015). "Signal denoising via quadratic semi-infinite programming". In: 2015 49th Asilomar Conference on Signals, Systems and Computers. IEEE, pp. 612-616.
De Hemptinne, C. et al. (2015). "Therapeutic deep brain stimulation reduces cortical phase-amplitude coupling in Parkinson's disease". In: Nature neuroscience 18.5, pp. 779-786.
Deshmukh, S.S. et al. (2010). "Theta modulation in the medial and the lateral entorhinal cortices". In: Journal of neurophysiology 104.2, pp. 994-1006.
Deuschl, G. et al. (2013). "Subthalamic neurostimulation for Parkinson's disease with early fluctuations: balancing the risks and benefits". In: The Lancet Neurology 12.10, pp. 1025-1034.
Deuschl, G. et al. (2006). "A randomized trial of deep-brain stimulation for Parkinson's disease". In: New England Journal of Medicine 355.9, pp. 896-908.
Diaconescu, E. (2008). "The use of NARX neural networks to predict chaotic time series". In: Wseas Transactions on computer research 3.3, pp. 182-191.

(56) References Cited

OTHER PUBLICATIONS

Dostrovsky, J.O. et al. (2002). "Mechanisms of deep brain stimulation". In: Movement disorders: official journal of the Movement Disorder Society 17.S3, S63-S68.
Eichenbaum, H. et al. (1996). "Functional organization of the hippocampal memory system". In: Proceedings of the National Academy of Sciences 93.24, pp. 13500-13507.
Eichenbaum, H. et al. (2007). "The medial temporal lobe and recognition memory". In: Annu. Rev. Neurosci. 30, pp. 123-152.
Ekstrom, A.D. (2021). "Regional variation in neurovascular coupling and why we still lack a Rosetta Stone". In: Philosophical Transactions of the Royal Society B 376.1815, 12 pages.
Stone, S.S. et al. (2011). "Functional convergence of developmentally and adult-generated granule cells in dentate gyrus circuits supporting hippocampus-dependent memory". In: Hippocampus 21.12, pp. 1348-1362.
Suthana, N. et al. (2012). "Memory enhancement and deep-brain stimulation of the entorhinal area". In: New England Journal of Medicine 366.6, pp. 502-510.
Tinkhauser, G. et al. (2017). "The modulatory effect of adaptive deep brain stimulation on beta bursts in Parkinson's disease". In: Brain 140.4, pp. 1053-1067.
Toda, H. et al. (2008). "The regulation of adult rodent hippocampal neurogenesis by deep brain stimulation". In: Journal of neurosurgery 108.1, pp. 132-138.
Tort, A.B. et al. (2010). "Measuring phase-amplitude coupling between neuronal oscillations of different frequencies". In: Journal of neurophysiology 104.2, pp. 1195-1210.
Tort, A.B. et al. (2009). "Theta-gamma coupling increases during the learning of item-context associations". In: Proceedings of the National Academy of Sciences 106.49, pp. 20942-20947.
Tsao, A. et al. (2018). "Integrating time from experience in the lateral entorhinal cortex". In: Nature 561.7721, pp. 57-62.
Tsuda, M. et al. (2014). "Analysis and identification of the EEG signals from visual stimulation". In: Procedia Computer Science 35, pp. 1292-1299.
Tulleken, H.J. (1990). "Generalized binary noise test-signal concept for improved identification-experiment design". In: Automatica 26.1, pp. 37-49.
Tulleken, H. (1988). "A generalised binary noise test-signal concept for improved identification-experiment design". In: IFAC Proceedings vols. 21.9, pp. 577-585.
Tulving, E. (1972). "12. Episodic and Semantic Memory". In: Organization of memory/Eds E. Tulving, W. Donaldson, NY: Academic Press, pp. 381-403.
Tulving, E. (1983). "Elements of episodic memory". Oxford University Press 1983, Abstract, 1 page, ISBN(s) 9780198521259 0198521251 0198521022 0199534691.
Tulving, E. (2002). "Episodic memory: From mind to brain". In: Annual review of psychology 53.1, pp. 1-25.
Turnbull, I. M. et al. (1985). "Stimulation of the basal nucleus of Meynert in senile dementia of Alzheimer's type". In: Stereotactic and Functional Neurosurgery 48.1-6, pp. 216-221.
Umbach, G. et al. (2020). "Time cells in the human hippocampus and entorhinal cortex support episodic memory". In: bioRxiv.
Ziegler, J.G. et al. (1942). "Optimum settings for automatic controllers". In: trans. ASME 64.11.
Vaz, A.P. et al. (2017). "Dual origins of measured phase-amplitude coupling reveal distinct neural mechanisms underlying episodic memory in the human cortex". In: Neuroimage 148, pp. 148-159.
Vidal, J.J. (1977). "Real-time detection of brain events in EEG". In: Proceedings of the IEEE 65.5, pp. 633-641.
Vidal, J.J. et al. (1973). "Toward direct brain-computer communication". In : Annual Reviews Biophys. Bioeng. vol. 2, pp. 157-180.
Vugt, M. K. van et al. (2010). "Hippocampal gamma oscillations increase with memory load". In: Journal of Neuroscience 30.7, pp. 2694-2699.
Wagner, A.D. et al. (2005). "Parietal lobe contributions to episodic memory retrieval". In: Trends in cognitive sciences 9.9, pp. 445-453.
Wang, D.X. et al. (2019). "Subspace averaging of auditory evoked potentials". In: 2019 41st Annual International Conference of the IEEE Engineering in Medicine and Biology Society (EMBC). IEEE, pp. 656-659.
Wang, D.X. et al. (2021). "Cross-regional phase amplitude coupling supports the encoding of episodic memories". In: Hippocampus 31.5, pp. 481-492.
Watrous, A.J. et al. (2013). "A comparative study of human and rat hippocampal low-frequency oscillations during spatial navigation". In: Hippocampus 23.8, pp. 656-661.
Wechsler, D. (1945). "Wechsler memory scale." In : Psychological Corporation, Psycnet.apa.org, 1 page.
Wheeler, M.A. et al. (1995). "Frontal lobe damage produces episodic memory impairment". In: Journal of the International Neuropsychological Society 1.6, pp. 525-536.
Wheeler, M.A. et al. (1997). "Toward a theory of episodic memory: the frontal lobes and autonoetic consciousness." In: Psychological bulletin 121.3, p. 331.
Witter, M.P. et al. (2000). "Anatomical organization of the parahippocampal-hippocampal network". In: Annals of the New York Academy of Sciences 911.1, pp. 1-24.
Xie, H. et al. (2009). "Time series prediction based on NARX neural networks: An advanced approach". In: 2009 International conference on machine learning and cybernetics. vol. 3. IEEE, pp. 1275-1279.
Yang, Y. et al. (2018). "A control-theoretic system identification framework and a real-time closed-loop clinical simulation testbed for electrical brain stimulation". In: Journal of neural engineering 15.6, p. 066007.
Yang, Y., S. Qiao, et al. (2021). "Modelling and prediction of the dynamic responses of large-scale brain networks during direct electrical stimulation". In: Nature biomedical engineering 5.4, pp. 324-345.
Yao, M. et al. (2021). "Temporal-wise Attention Spiking Neural Networks for Event Streams Classification". In: Proceedings of the IEEE/CVF International Conference on Computer Vision, pp. 10221-10230.
Yonelinas, A.P. et al. (2005). "Separating the brain regions involved in recollection and familiarity in recognition memory". In: Journal of Neuroscience 25.11, pp. 3002-3008.
Young, T. et al. (2018). "Recent trends in deep learning based natural language processing". IEEEE Computational intelligenCe magazine 13.3, pp. 55-75.
Zelmann, R. et al. (2020). "CLoSES: A platform for closed-loop intracranial stimulation in humans". In: NeuroImage 223, p. 117314.
Zhang, H. et al. (2015). "Traveling theta waves in the human hippocampus". In: Journal of Neuroscience 35.36, pp. 12477-12487.
Zhou, C. et al. (2018). "A systematic review and meta-analysis of deep brain stimulation in treatment-resistant depression". In: Progress in Neuro-Psychopharmacology and Biological Psychiatry 82, pp. 224-232.
Ngo, H.-V.V. et al. (2013). "Auditory closed-loop stimulation of the sleep slow oscillation enhances memory". In: Neuron 78.3, pp. 545-553.
Nolde, S.F. et al (1998). "The role of prefrontal cortex during tests of episodic memory". In: Trends in cognitive sciences 2.10, pp. 399-406.
Norman, K.A. et al. (2003). "Modeling hippocampal and neocortical contributions to recognition memory: a complementary-learning-systems approach." In: Psychological review 110.4, p. 611.
Nune, G. et al. (2019). "Treatment of drug-resistant epilepsy in patients with periventricular nodular heterotopia using RNS® System: Efficacy and description of chronic electrophysiological recordings". In: Clinical Neurophysiology 130.8, pp. 1196-1207.
Nyhus, E. and T. Curran (2010). "Functional role of gamma and theta oscillations in episodic memory". In: Neuroscience & Biobehavioral Reviews 34.7, pp. 1023-1035.
Ojemann, G.A. et al. (2013). "Relation between functional magnetic resonance imaging (fMRI) and single neuron, local field potential (LFP) and electrocorticography (ECoG) activity in human cortex". In: Frontiers in human neuroscience 7, p. 34.

(56) References Cited

OTHER PUBLICATIONS

Onslow, A.C. et al. (2011). "Quantifying phase-amplitude coupling in neuronal network oscillations". In: Progress in biophysics and molecular biology 105.1-2, pp. 49-57.
Oppenheim, A.V. et al. (1989). Discrete-Time Signal Processing. Prentice Hall.
Oppenheim, A.V. et al. (1997). Fourier series representation of periodic signals. Prentice Hall.
Osipova, D. et al. (2006). "Theta and gamma oscillations predict encoding and retrieval of declarative memory". In: Journal of neuroscience 26.28, pp. 7523-7531.
Oxley, T.J. et al. (2016). "Minimally invasive endovascular stent-electrode array for high-fidelity, chronic recordings of cortical neural activity". In: Nature biotechnology 34.3, pp. 320-327.
Oxley, T.J. et al. (2021). "Motor neuroprosthesis implanted with neurointerventional surgery improves capacity for activities of daily living tasks in severe paralysis: first in-human experience". In: Journal of neurointerventional surgery 13.2, pp. 102-108.
Paller, K.A. et al. (2002). "Observing the transformation of experience into memory". In: Trends in cognitive sciences 6.2, pp. 93-102.
Perlmutter, J.S. et al. (2006). "Deep brain stimulation". In: Annu. Rev. Neurosci. 29, pp. 229-257.
Pinheiro, J.C. et al. (1996). "Unconstrained parametrizations for variance-covariance matrices". In: Statistics and computing 6.3, pp. 289-296.
Poppenk, J. et al. (2013). "Long-axis specialization of the human hippocampus". In: Trends in cognitive sciences 17.5, pp. 230-240.
Pradhan, C. et al. (2012). "Higher-order spectrum in understanding nonlinearity in EEG rhythms". In: Computational and mathematical methods in medicine 2012.
Preston, A.R. et al. (2013). "Interplay of hippocampus and prefrontal cortex in memory". In: Current Biology 23.17, R764-R773.
Price, G.W. et al. (2012). "System identification of the EEG transformation due to TMS pulses: a novel method for a synchronous brain computer interface." In: 2012 Spring Congress on Engineering and Technology. IEEE, pp. 1-5.
Rami, M.A. et al. (2000). "Linear matrix inequalities, Riccati equations, and indefinite stochastic linear quadratic controls". In: IEEE Transactions on Automatic Control 45.6, pp. 1131-1143.
Ranganath, C. et al. (2012). "Two cortical systems for memory-guided behaviour". In: Nature Reviews Neuroscience 13.10, pp. 713-726.
Richman, J.S. et al. (2000). "Physiological time-series analysis using approximate entropy and sample entropy". In: American Journal of Physiology-Heart and Circulatory Physiology 278.6, H2039-H2049.
Ritchey, M. et al. (2015). "Cortico-hippocampal systems involved in memory and cognition: the PMAT framework". In: Progress in brain research. vol. 219. Elsevier, pp. 45-64.
Robinson, J. et al. (2016). "Optogenetic activation of septal glutamatergic neurons drive hippocampal theta rhythms". In: Journal of Neuroscience 36.10, pp. 3016-3023.
Rosenblum, M.G. et al. (2004). "Controlling synchronization in an ensemble of globally coupled oscillators". In: Physical Review Letters 92.11, p. 114102.
Rutishauser, U. et al. (2010). "Human memory strength is predicted by theta-frequency phase-locking of single neurons". In: Nature 464.7290, p. 903.
Rutishauser, U. et al. (2015). "Representation of retrieval confidence by single neurons in the human medial temporal lobe". In: Nature neuroscience 18.7, pp. 1041-1050.
Santaniello, S. et al. (2015). "Therapeutic mechanisms of high-frequency stimulation in Parkinson's disease and neural restoration via loop-based reinforcement". In: Proceedings of the National Academy of Sciences 112.6, E586-E595.
Schlichting, M.L. et al. (2015). "Memory integration: neural mechanisms and implications for behavior". In: Current opinion in behavioral sciences 1, pp. 1-8.
Schomburg, E.W. et al. (2014). "Theta phase segregation of input-specific gamma patterns in entorhinal-hippocampal networks". In: Neuron 84.2, pp. 470-485.
Scoville, W.B. et al. (1957). "Loss of recent memory after bilateral hippocampal lesions". In: Journal of neurology, neurosurgery, and psychiatry 20.1, p. 11.
Sederberg, P.B. et al. (2006). "Oscillatory correlates of the primacy effect in episodic memory". In: NeuroImage 32.3, pp. 1422-1431.
Sederberg, P.B. et al. (2003a). "Theta and gamma oscillations during encoding predict subsequent recall". In: Journal of Neuroscience 23.34, pp. 10809-10814.
Sederberg, P.B. et al. (2003b). "Theta and gamma oscillations during encoding predict subsequent recall". In: Journal of Neuroscience 23.34, pp. 10809-10814.
Sederberg, P.B. et al. (2007). "Hippocampal and neocortical gamma oscillations predict memory formation in humans". In: Cerebral Cortex 17.5, pp. 1190-1196.
Shallice, T. et al. (1970). "Independent functioning of verbal memory stores: A neuropsychological study". In: The Quarterly journal of experimental psychology 22.2, pp. 261-273.
Zion-Golumbic, E. et al. (2010). "Neural dynamics associated with semantic and episodic memory for faces: evidence from multiple frequency bands". In: Journal of Cognitive Neuroscience 22.2, pp. 263-277.
Shirvalkar, P.R. et al. (2010). "Bidirectional changes to hippocampal theta-gamma comodulation predict memory for recent spatial episodes". In: Proceedings of the National Academy of Sciences 107.15, pp. 7054-7059.
Siapas, A.G. et al. (2005). "Prefrontal phase locking to hippocampal theta oscillations". In: Neuron 46.1, pp. 141-151.
Skarpaas, T.L. et al. (2019). "Brain-responsive neurostimulation for epilepsy (RNS® System)". In: Epilepsy research 153, pp. 68-70.
Solomon, E. et al. (2017). "Widespread theta synchrony and high-frequency desynchronization underlies enhanced cognition". In: Nature communications 8.1, pp. 1-14.
Sols, I. et al. (2017). "Event boundaries trigger rapid memory reinstatement of the prior events to promote their representation in long-term memory". In: Current Biology 27.22, pp. 3499-3504.
Squire, L.R. (1992). "Memory and the hippocampus: a synthesis from findings with rats, monkeys, and humans." In: Psychological review 99.2, p. 195.
Sritharan, D. et al. (2014). "Fragility in dynamic networks: application to neural networks in the epileptic cortex". In: Neural computation 26.10, pp. 2294-2327.
Stam, C. et al. (1996). "Diagnostic usefulness of linear and non-linear quantitative EEG analysis in Alzheimer's disease". In: Clinical Electroencephalography 27.2, pp. 69-77.
Stam, C.J. (2005). "Nonlinear dynamical analysis of EEG and MEG: review of an emerging field". In: Clinical neurophysiology 116.10, pp. 2266-2301.
Staudigl, T. et al. (2013). "Theta oscillations at encoding mediate the context-dependent nature of human episodic memory". In: Current biology 23.12, pp. 1101-1106.
Steinvorth, S. et al. (2010). "Human entorhinal gamma and theta oscillations selective for remote autobiographical memory". In: Hippocampus 20.1, pp. 166-173.
Stephan, K.E. et al. (2010). "Ten simple rules for dynamic causal modeling". In: Neuroimage 49.4, pp. 3099-3109.
Stone, S.S. et al. (2011). "Stimulation of entorhinal cortex promotes adult neurogenesis and facilitates spatial memory". In: Journal of Neuroscience 31.38, pp. 13469-13484.
Ekstrom, A.D. et al. (2005). "Human hippocampal theta activity during virtual navigation". In: Hippocampus 15.7, pp. 881-889.
Elger, C. et al. (2000). "Nonlinear EEG analysis and its potential role in epileptology". In: Epilepsia 41, S34-S38.
Eykhoff, P. et al. (1974). System identification. vol. 14. Wiley London.
Ezzyat, Y. et al. (2018). "Closed-loop stimulation of temporal cortex rescues functional networks and improves memory". In: Nature communications 9.1, pp. 1-8.
Feldman, D.E. (2012). "The spike-timing dependence of plasticity". In: Neuron 75.4, pp. 556-571.

(56) References Cited

OTHER PUBLICATIONS

Fell, J. et al. (2011). "Medial temporal theta/alpha power enhancement precedes successful memory encoding: evidence based on intracranial EEG". In: Journal of Neuroscience 31.14, pp. 5392-5397.
Fisher, R. et al. (2010). "Electrical stimulation of the anterior nucleus of thalamus for treatment of refractory epilepsy". In: Epilepsia 51.5, pp. 899-908.
Fletcher, P. et al. (1998). "The functional roles of prefrontal cortex in episodic memory. I. Encoding." In: Brain: a journal of neurology 121.7, pp. 1239-1248.
Foresee, F.D. et al. (1997). "Gauss-Newton approximation to Bayesian learning". In: Proceedings of international conference on neural networks (ICNN'97). vol. 3. IEEE, pp. 1930-1935.
Foster, B.L. et al. (2012). "Resting oscillations and cross-frequency coupling in the human posteromedial cortex". In: Neuroimage 60.1, pp. 384-391.
Franck, G. et al. (1985). "Identification of a large water-heated crossflow heat exchanger with binary multifrequency signals". In: IFAC Proceedings vols. 18.5, pp. 1859-1864.
Fries, P. (2005). "A mechanism for cognitive dynamics: neuronal communication through neuronal coherence". In: Trends in cognitive sciences 9.10, pp. 474-480.
Fries, P (2009). "Neuronal gamma-band synchronization as a fundamental process in cortical computation". In: Annual review of neuroscience 32, pp. 209-224.
Friston, K. et al. (1997). "Psychophysiological and modulatory interactions in neuroimaging". In: Neuroimage 6.3, pp. 218-229.
Furtak, S.C. et al. (2007). "Functional neuroanatomy of the parahippocampal region in the rat: the perirhinal and postrhinal cortices". In: Hippocampus 17.9, pp. 709-722.
Galassi, A. et al. (2020). "Attention in natural language processing". In: IEEE Transactions on Neural Networks and Learning Systems 32.10, pp. 4291-4308.
Gatt, A. et al. (2018). "Survey of the state of the art in natural language generation: Core tasks, applications and evaluation". In: Journal of Artificial Intelligence Research 61, pp. 65-170.
Gershenfeld, N.A. et al. (1993). The future of time series. Xerox Corporation, Palo Alto Research Center Palo Alto, CA, USA.
Gillund, G. (2012). "Episodic Memory". In: Encyclopedia of Human Behavior (Second Edition). Ed. by V. Ramachandran. Second Edition. San Diego: Academic Press, pp. 68-72. url: https://www.sciencedirect.com/science/article/pii/B978012375000600152X.
Glanzer, M. et al. (1966). "Two storage mechanisms in free recall". In: Journal of verbal learning and verbal behavior 5.4, pp. 351-360.
Golub, G.H. et al. (1996). Matrix Computations. Third. The Johns Hopkins University Press.
Gordon, B. et al. (1990). "Parameters for direct cortical electrical stimulation in the human: histopathologic confirmation". In: Electroencephalography and clinical neurophysiology 75.5, pp. 371-377.
Goyal, A. et al. (2020). "Functionally distinct high and low theta oscillations in the human hippocampus". In: Nature communications 11.1, pp. 1-10.
Greenberg, B. D. et al. (2006). "Three-year outcomes in deep brain stimulation for highly resistant obsessive-compulsive disorder". In: Neuropsychopharmacology 31.11, pp. 2384-2393.
Greiser, S. et al. (2015). "Results of the pilot assistance system"Assisted Low-Level Flight and Landing on Unprepared Landing Sites" obtained with the ACT/FHS research rotorcraft". In: Aerospace Science and Technology 45, pp. 215-227.
Griffiths, B. J. et al. (2019). "Directional coupling of slow and fast hippocampal gamma with neocortical alpha/beta oscillations in human episodic memory". In: Proceedings of the National Academy of Sciences 116.43, pp. 21834-21842.
Halevi, Y. (1994). "Stable LQG controllers". In: IEEE Transactions on Automatic Control 39.10, pp. 2104-2106.
Han, Y. et al. (2021). "Dynamic neural networks: A survey". In: IEEE Transactions on Pattern Analysis and Machine Intelligence.
Hasselmo, M.E. (2005). "What is the function of hippocampal theta rhythm ?—Linking behavioral data to phasic properties of field potential and unit recording data". In: Hippocampus 15.7, pp. 936-949.
Hasselmo, M.E. (2011). How we remember: brain mechanisms of episodic memory. MIT press.
Hasselmo, M.E. et al. (2002). "A proposed function for hippocampal theta rhythm: separate phases of encoding and retrieval enhance reversal of prior learning". In: Neural computation 14.4, pp. 793-817.
Henderson, C.R. (1973). "Sire evaluation and genetic trends". In: Journal of Animal Science 1973.Symposium, pp. 10-41.
Henderson, I. et al. (1989). "Maxent binary identification of a warm air system". In: IMEKO Symposium on Microprosessors in Temperature and Thermal Measurement.
Herweg, N.A. et al. (2020). "Theta oscillations in human memory". In: Trends in cognitive sciences 24.3, pp. 208-227.
Hescham, S. et al. (2013). "Deep brain stimulation of the forniceal area enhances memory functions in experimental dementia: the role of stimulation parameters". In: Brain stimulation 6.1, pp. 72-77.
Hickey, P. et al. (2016). "Deep brain stimulation: a paradigm shifting approach to treat Parkinson's disease". In: Frontiers in neuroscience, p. 173.
Hill, P.F. et al. (2020). "Comparison of fMRI correlates of successful episodic memory encoding in temporal lobe epilepsy patients and healthy controls". In: Neuroimage 207, p. 116397.
Hill, P.F. et al. (2021). "Distinct neurophysiological correlates of the fMRI BOLD signal in the hippocampus and neocortex". In: Journal of Neuroscience 41.29, pp. 6343-6352.
Hoang, K. B. et al. (2017). "Biomarkers and stimulation algorithms for adaptive brain stimulation". In: Frontiers in Neuroscience 11, p. 564.
Hodgkin, A.L. et al. (1952). "A quantitative description of membrane current and its application to conduction and excitation in nerve". In: The Journal of physiology 117.4, p. 500.
Hornberger, M. et al. (2012). "Episodic memory in frontotemporal dementia: a critical review". In: Brain 135.3, pp. 678-692.
Hyman, J.M. et al. (2005). "Medial prefrontal cortex cells show dynamic modulation with the hippocampal theta rhythm dependent on behavior". In: Hippocampus 15.6, pp. 739-749.
Insausti, R. et al. (2019). "Cytoarchitectonic Areas of the Gyrus ambiens in the Human Brain". In: Frontiers in neuroanatomy 13, p. 21.
Izhikevich, E.M. (2007). Dynamical systems in neuroscience. MIT press.
Jacobs, J. (2014). "Hippocampal theta oscillations are slower in humans than in rodents: implications for models of spatial navigation and memory". In: Philosophical Transactions of the Royal Society B: Biological Sciences 369.1635, p. 20130304.
Jacobs, J. et al. (2017). "Human hippocampal theta oscillations: distinctive features and interspecies commonalities". In: The hippocampus from cells to systems. Springer, pp. 37-67.
Jacobs, J. et al. (2016). "Direct electrical stimulation of the human entorhinal region and hippocampus impairs memory". In: Neuron 92.5, pp. 983-990.
Jansen, B.H. et al. (1995). "Electroencephalogram and visual evoked potential generation in a mathematical model of coupled cortical columns". In: Biological cybernetics 73.4, pp. 357-366.
Jantz, J. et al. (2017). "A brain-computer interface for extended reality interfaces". In: ACM SIGGRAPH 2017 VR Village, pp. 1-2.
Jensen, O. et al. (2000). "Position reconstruction from an ensemble of hippocampal place cells: contribution of theta phase coding". In: Journal of neurophysiology 83.5, pp. 2602-2609.

* cited by examiner

SYSTEM AND METHOD FOR DEEP BRAIN STIMULATION

CROSS-REFERENCE TO RELATED APPLICATION

This application claims priority to U.S. Provisional Patent Application Ser. No. 63/383,127, filed Nov. 10, 2022, and titled "SYSTEM AND METHOD FOR DEEP BRAIN STIMULATION," which is incorporated by reference herein in its entirety.

ACKNOWLEDGEMENT OF GOVERNMENT SUPPORT

This invention was made with government support under NS107357 awarded by the National Institutes of Health. The government has certain rights in the invention.

BACKGROUND

1. Field

The present application relates generally to deep brain stimulation and, more particularly, to a system and method of closed-loop control of deep brain stimulation.

2. Discussion of Related Art

Deep brain stimulation (DBS) with neuromodulation technique is an effective treatment for neurodegenerative disorders such as epilepsy, Parkinson's disease, post-traumatic amnesia, Alzheimer's disease, and neuropsychiatric disorders, such as, depression, obsessive-compulsive disorder, and schizophrenia. Typically, the neuromodulation strategies for neuromotor disorders utilize open-loop control, which relies solely on preset empirically derived stimulation parameters from clinical trials. However, unlike movement disorders, the underlying brain circuitry for memory disorders is more sophisticated and requires investigation of brain activity patterns or biomarkers as neuro-feedback to govern subsequent stimulation parameters. Open-loop schemes fail to capture the drastically changing dynamics of the neurological activities associated with cognitive processes, and some have been found to actually impair memory performance. In contrast, closed-loop stimulation systems that use data-driven models, such as, machine learning classifier triggered stimulation systems that deliver stimuli when the classifier predicts a memory failure. However, these systems are not accurate in modeling the input-output dynamics between posterior cingulate cortex (PCC) applied stimulation and stimuli-evoked hippocampal theta and gamma power. These systems also lack effectiveness in modulating theta and gamma power to a desired target level. It is with these observations in mind, among others, that various aspects of the present disclosure were conceived and developed.

BRIEF SUMMARY

The present inventive concept addresses the foregoing problems by providing a method and system for deep brain stimulation. In one implementation, a method for deep brain stimulation includes recording, via intracranial electrodes, electrical signals in a hippocampus region of a brain, the electrical signals including biomarkers related to memory encoding; receiving, via a controller, the electrical signals including the biomarkers; modulating, via the controller, an input/output (I/O) relationship between the biomarkers and electrical stimuli applied to a posterior cingulate cortex (PCC) of the brain; and stimulating, via the controller and a neurostimulator, the PCC based on the I/O relationship to achieve a desired level of the biomarkers.

In another implementation, a system for deep brain stimulation is described and claimed herein. The system includes intracranial electrodes operable to be disposed in a hippocampus region of a brain and configured to record electrical signals that include biomarkers related to memory encoding; a neurostimulator configured to stimulate a posterior cingulate cortex (PCC) of the brain; and a controller configured to receive the electrical signals and modulating an input/output (I/O) relationship between the biomarkers and electrical stimuli applied to a posterior cingulate cortex (PCC) of the brain by controlling the neurostimulator to stimulate the PCC based on the I/O relationship to achieve a desired level of the biomarkers.

Additional aspects, advantages, and utilities of the present inventive concept will be set forth, in part, in the description which follows and, in part, will be obvious from the description, or may be learned by practice of the present inventive concept.

The foregoing is intended to be illustrative and is not meant in a limiting sense. Many features and subcombinations of the present inventive concept may be made and will be readily evident upon a study of the following specification and accompanying drawings comprising a part thereof. These features and subcombinations may be employed without reference to other features and subcombinations.

BRIEF DESCRIPTION OF THE DRAWINGS

The description will be more fully understood with reference to the following figures and data graphs, which are presented as various embodiments of the present inventive concept and should not be construed as a complete recitation of the scope of the present inventive concept, wherein.

Figure 1:
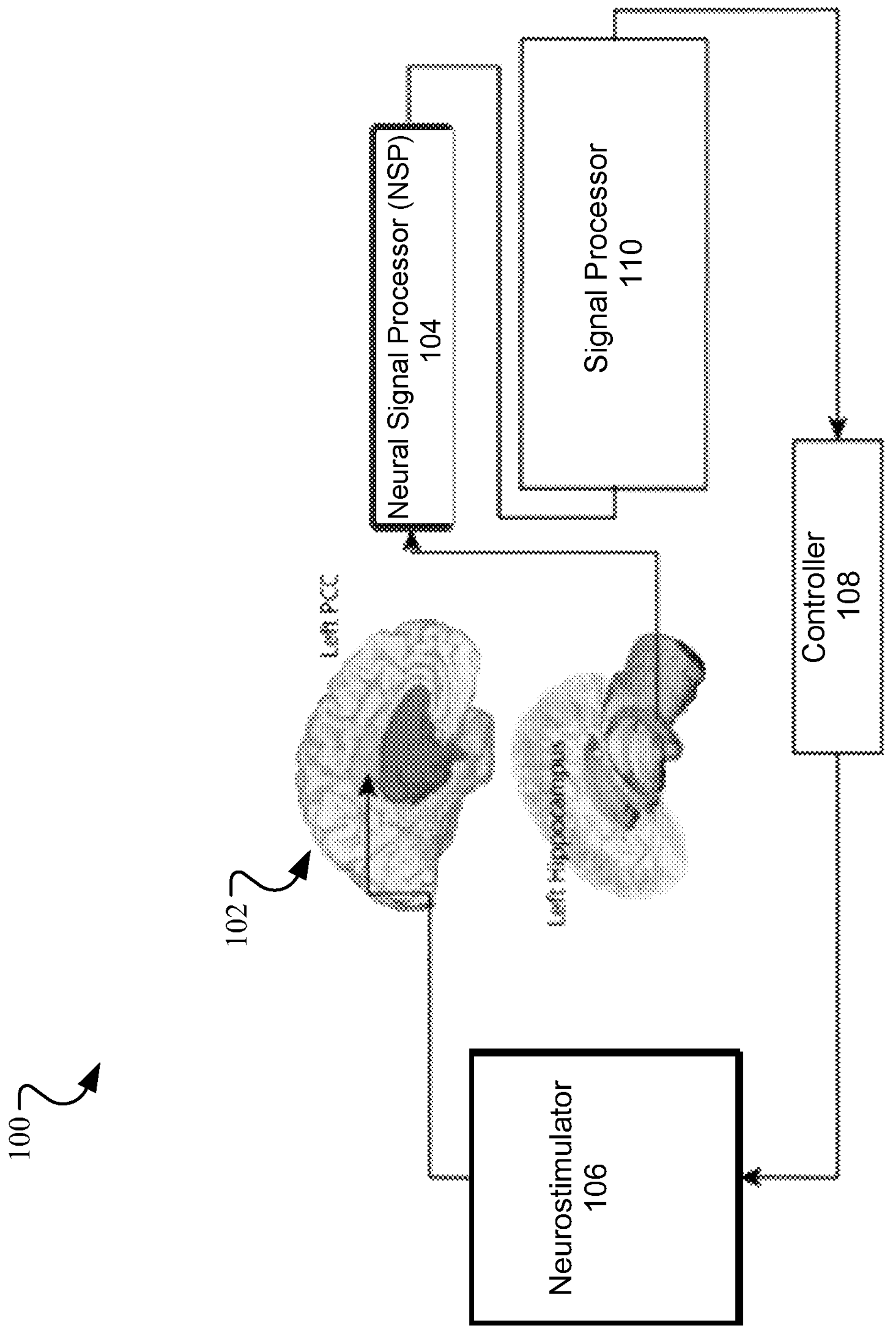
FIG. 1 shows an example system for deep brain stimulation.

The drawing figures do not limit the present inventive concept to the specific embodiments disclosed and described herein. The drawings are not necessarily to scale, emphasis instead being placed on clearly illustrating principles of certain embodiments of the present inventive concept.

DETAILED DESCRIPTION

The following detailed description references the accompanying drawings that illustrate various embodiments of the present inventive concept. The illustrations and description are intended to describe aspects and embodiments of the present inventive concept in sufficient detail to enable those skilled in the art to practice the present inventive concept. Other components can be utilized, and changes can be made without departing from the scope of the present inventive concept. The following description is, therefore, not to be taken in a limiting sense. The scope of the present inventive concept is defined only by the appended claims, along with the full scope of equivalents to which such claims are entitled.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

Any term of degree such as, but not limited to, "substantially" as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The terms "comprising," "including" and "having" are used interchangeably in this disclosure. The terms "comprising," "including" and "having" mean to include, but not necessarily be limited to the things so described.

Lastly, the terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps, or acts are in some way inherently mutually exclusive.

II. General Architecture

To begin a detailed description of an example system 100, reference is made to FIGS. 1-5. In one implementation, the system 100 includes intracranial electrodes disposed in a hippocampus region of a brain 102 and configured to record electrical signals using a neural signal processor (NSP) 104. The system 100 further includes a neurostimulator 106 configured to stimulate a posterior cingulate cortex (PCC) of the brain 102, and a controller 108 configured to receive the electrical signals and modulate an input/output (I/O) relationship between the biomarkers and electrical stimuli applied to a posterior cingulate cortex (PCC) of the brain 102 by controlling the neurostimulator 106 to stimulate the PCC based on the I/O relationship to achieve a desired level of the biomarkers. In an implementation, the electrical signals are denoised and processed by a signal processor 110 to extract the biomarkers before being received by the controller 108.

The NSP 104 utilizes intracranial electrodes disposed in a hippocampus region of a brain 102 to record electrical signals therein. In an implementation the electrical signals are acquired using intracranial electroencephalogram (iEEG). The electrical signals include biomarkers, such as, hippocampal theta and gamma oscillatory power, which are related to memory encoding.

The neurostimulator 106 is controlled via the controller 108 to stimulate the PCC of the brain 102 to modulate the changes in hippocampal oscillatory power. In an implementation, the neurostimulator 106 stimulates the PCC using binary-noise (BN) stimulation. Stimulating the posterior cingulate cortex (PCC) results in increases in hippocampal gamma power and conveys dynamical changes in the theta band.

The controller 108 receives the electrical signals recorded by the NSP 104 and modulates an input/output (I/O) relationship between the biomarkers and electrical stimuli applied to a posterior cingulate cortex (PCC) of the brain 102 by controlling the neurostimulator 106 to stimulate the PCC based on the I/O relationship to achieve a desired level of the biomarkers. The desired level of the biomarkers depends on certain memory-relevant biomarkers. A 50%-100% power increase, compared to the baseline, is considered desirable. For instance, this desired level could be between 80 to 120 microvolts for typical theta oscillations and 7 to 12 microvolts for typical gamma oscillations.

Figure 2:
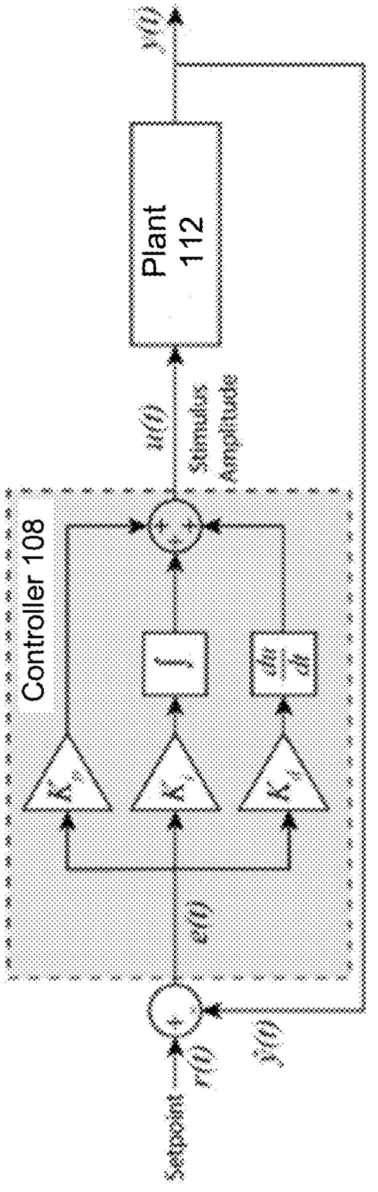
FIG. 2 shows an example proportional integral derivative (PID) controller of the system of FIG. 1.

In an implementation, the controller 108 is a non-model-based control mechanism proportional integral derivative (PID) controller, as illustrated in FIG. 2. In this implementation, the controller 108 is tuned for a plant 112. In this implementation the controller 108 adjusts the control signal by referencing the error e(t) between setpoint and feedback. The control function of the controller 108 is given by:

$$u(t) = K_p e(t) + K_i \int_0^t e(\tau)d(\tau) + K_d \frac{de(t)}{dt}$$

where $K_p$, $K_i$, and $K_d$ denote the gains for proportional, integral, and derivative terms, respectively.

In an implementation, the controller 108 is tuned to the plant 112 using the Ziegler-Nichols tuning method, where $K_i = K_p/T_i$ and $K_d = K_p T_d$, and where $T_i$ and $T_d$ are the integral and derivative time intervals, respectively. Thus, the control function of the controller 108 in this implementation is given by:

$$u(t) = K_p\left(e(t) + \frac{1}{T_i}\int_0^t e(\tau)d(\tau) + T_d \frac{de(t)}{dt}\right)$$

which has a transfer function of:

$$u(s) = K_p\left(1 + \frac{1}{T_i s} + T_d s\right)e(s) = K_p\left(\frac{T_d T_i s^2 + T_i s + 1}{T_i s}\right)e(s)$$

The Ziegler-Nichols' first sets $K_i$, and $K_d$ to zero and increases $K_p$ from zero until it reaches the ultimate gain $K_u$ at which the system outputs a stable and consistent oscillation, which has a period of $T_u$. Then, it adjusts the $T_i$ and $T_d$ based on the oscillation period $T_u$. Ziegler and Nichols gave a typical rule for solving the PID parameter once ultimate gain is achieved as illustrated in Table 1 below.

| Control Type | $K_p$ | $T_i$ | $T_d$ | $K_i$ | $K_d$ |
|---|---|---|---|---|---|
| P | $0.5K_u$ | — | — | — | — |
| PI | $0.45K_u$ | $0.80T_u$ | — | $0.54K_u/T_u$ | — |

-continued

| Control Type | $K_p$ | $T_i$ | $T_d$ | $K_i$ | $K_d$ |
|---|---|---|---|---|---|
| PD | $0.8K_u$ | — | $0.125T_u$. | — | $0.10K_uT_u$ |
| PID | $0.6K_u$ | $0.5T_u$ | $0.125T_u$. | $1.2K_u/T_u$ | $0.075K_uT_u$ |

Figure 3:
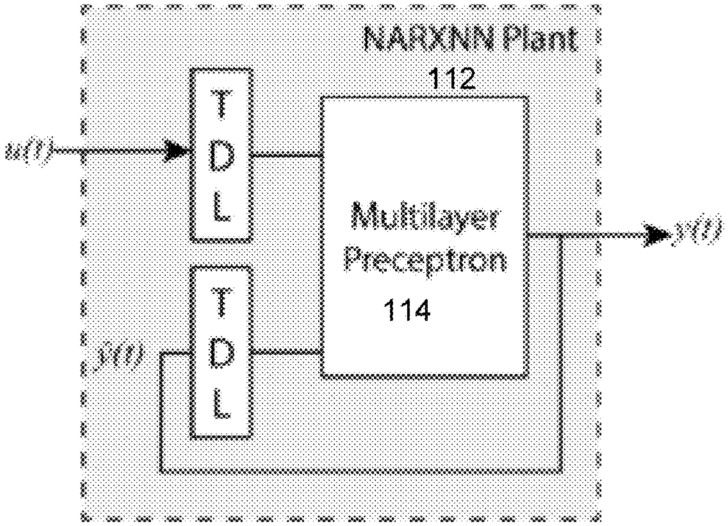
FIG. 3 shows an example nonlinear autoregressive with exogenous input neural network (NARXNN) plant for training the controller of FIG. 1.
Figure 4:
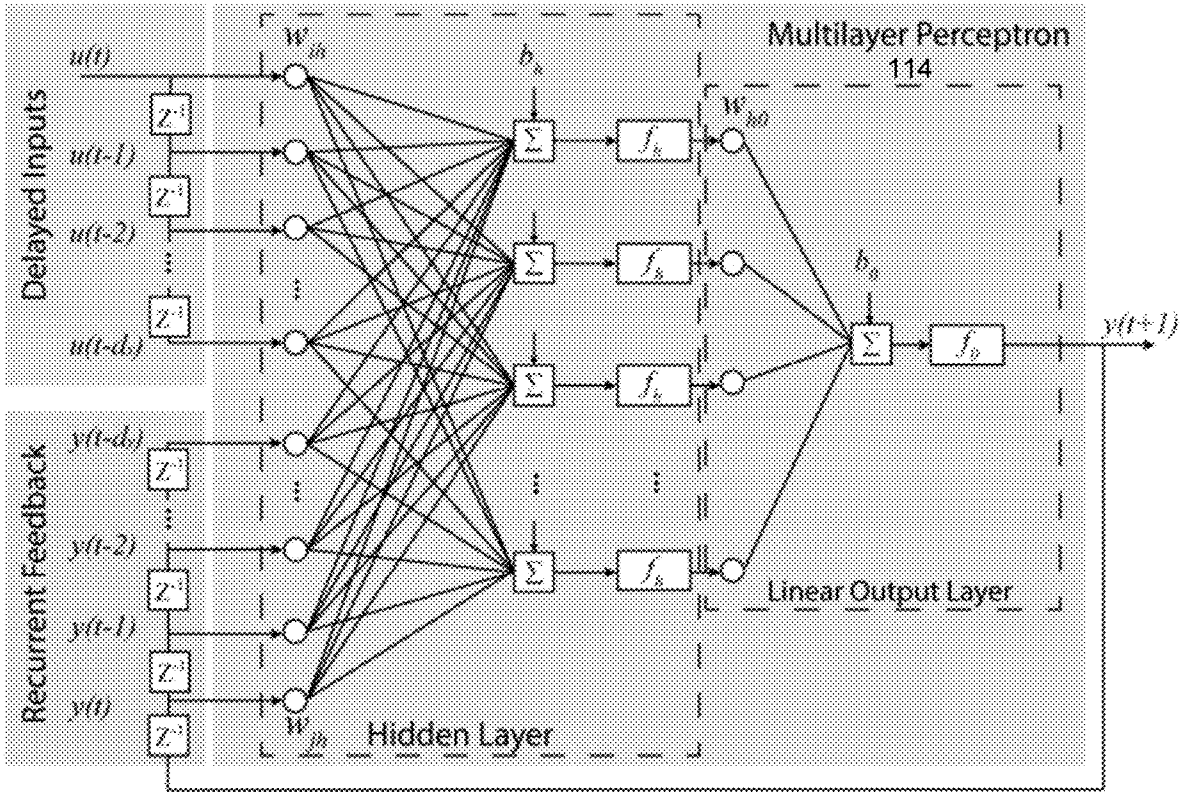
FIG. 4 shows a multilayer perceptron (MLP) neural network for use with the plant of FIG. 3.

In an implementation the plant is a nonlinear autoregressive with exogenous input neural network (NARXNN), as illustrated in FIGS. 3 and 4. In an implementation, the NARXNN includes a linear autoregressive with exogenous input (ARX) model with nonlinear activation function optimized by a multilayer perceptron (MLP) neural network 114 arranged in a structure having less than three layers. In another implementation, the NARXNN is a two-layer NARXNN having a hidden layer and an output layer for modeling hippocampal theta and gamma oscillatory power, as illustrated in FIG. 4. In an implementation, the architecture of the NARXNN plant is represented as:

$$y(t+1) = f_0\left[b_0 + \sum_{h=1}^{Nh} w_{h0}\cdot f_h\left(b_h + \sum_{i=0}^{d_u} w_{ih}u(t-1) + \sum_{j=0}^{d_y} w_{jh}y(t-j)\right)\right]$$

where $w_{ih}$ and $w_{jh}$ are the weights in the hidden layer for delayed input and output, respectively, $b_h$ is the bias in the hidden layer, $w_{h0}$ and $b_0$ are the weights and bias for the output layer, and $f_0$ (linear) and $f_h$ (sigmoid) are the activation functions of the output and hidden layer, respectively.

Figure 6:
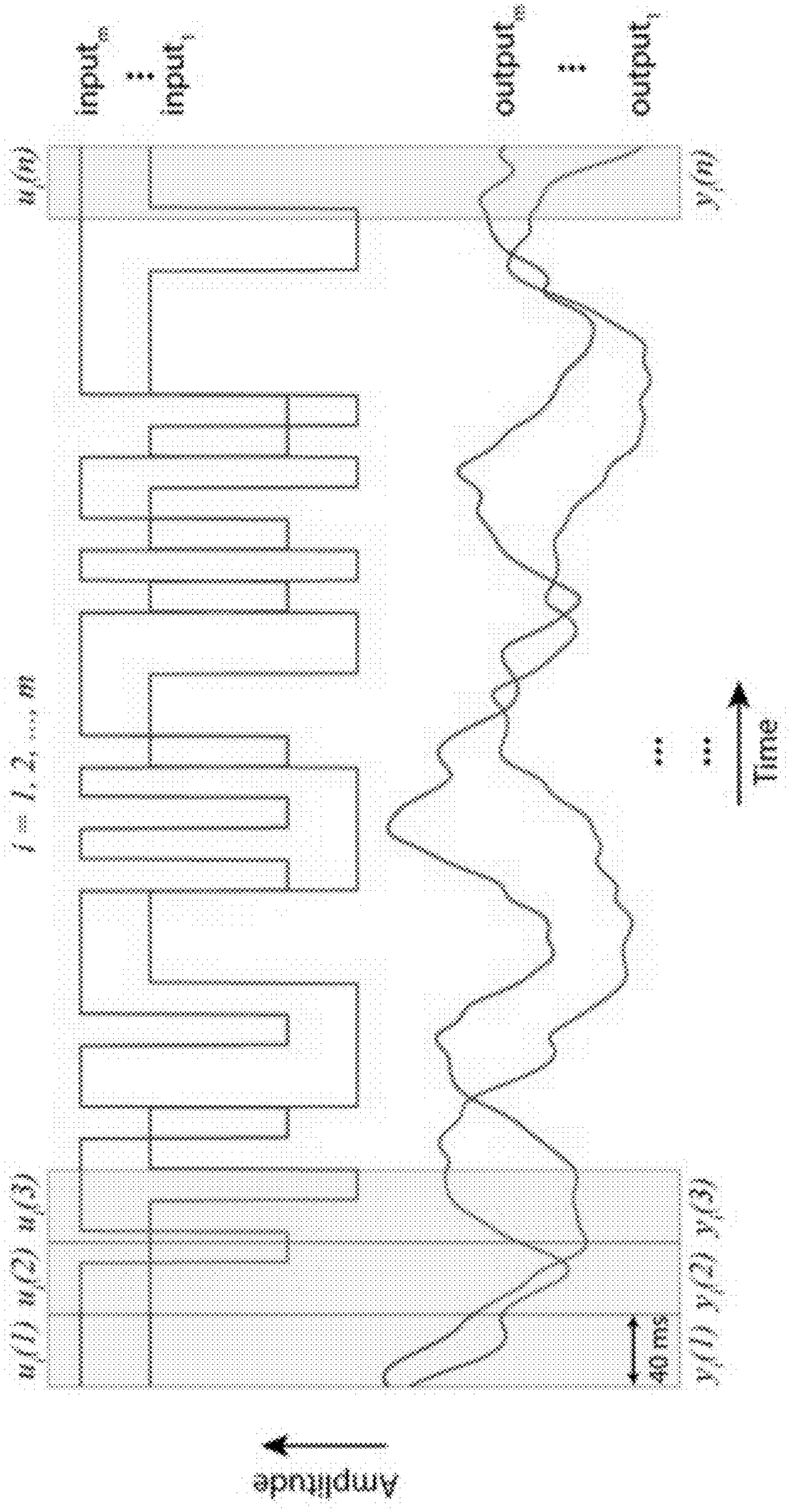
FIG. 6 shows an illustration of batching input/output data into segments using temporal-wise attention (TA) techniques.

Referring to FIG. 6, in an implementation, the plant 112 is fitted to the I/O data using multi-sequence training and temporal-wise attention (TA) techniques. The multi-sequence training is a network training procedure used when the time-series data is not available in one long sequence. Thus, each epoch back-propagates and optimizes the network parameters on a trial-to-trial basis by concatenating all the I/O trials, and the delay is reset for each trial to maintain the same temporal scheme (i.e. $y_i(t)$, . . . , $y_i(t\ d_y)$ and $u_i(t)$, . . . , $u_i(t\ d_u)$, i=1, 2, m. As illustrated in FIG. 6, the I/O trials are batched input TA segments. On discrete sample basis, the input is now $u_i=[u_i(1), u_i(2), \ldots, u_i(n)]$ where i=1, 2, 3, . . . , m is the number of trials for the subject, and the output is $y_i=[y_i(1), y_i(2), \ldots, y_i(n)]$, accordingly. Each batched sample consists of a 20-sample long feature (40 ms) such that $u_i(j)=[I_i((j-1)\times 20+1), I_i((j-1)\times 20+2), \ldots, I_i(j\times 20)]$ and $y_i(j)=[O_i((j-1)\times 20+1), O_i((j-1)\times 20+2), \ldots, O_i(j\times 20)]$, where $I_i$ and $O_i$ are the original I/O trials. In this implementation, a Bayesian regularization algorithm to minimize the squared error. The algorithm uses the Levenberg-Marquardt backpropagation, which computes the Jacobian matrix jw of the mean squared error (MSE) with respect to the weight and bias variables w. Each variable is adjusted according to:

$$jj = jw^T jw$$

$$je = jw^T E$$

$$dw = -(jj + I\mu)je$$

where E is the matrix of errors, I is the identity matrix, and the step size μ is adaptively increased until the epoch reduces the performance in minimizing the MSE. The Bayesian regularization prevents overfitting and to smooth the network response. The parameters of a network are considered as random variables and can be written as:

$$P\langle w|D|\alpha,\beta,M\rangle=\frac{P(D|w,\beta,M)P(D|w,\alpha,M)}{P(D|\alpha,\beta,M)}$$

where α and β are parameters for the objective function such that $E=\beta E_D+\alpha E_W$, where $E_W$ is the sum of squares of the network weights and $E_D$ is sum of squared errors $$E_D=\sum_{j=1}^{n}(y(j)-\hat{y}(j))^2.$$

D is the data set, M is the network model used, and w is the vector of network parameters. P (w|α, M) is the prior density representing the knowledge of the network parameter prior to any data collection. P (D|w, β, M) is the likelihood of the data occurring, given the parameter w. P (D|α, β, M) is a normalization factor with total probability of 1. The normalization factor can be solved by:

$$P(D|\alpha,\beta,M)=$$

$$\frac{P(D|w,\beta,M)P(w|\alpha,M)}{P\langle w|D|\alpha,\beta,M\rangle}=\frac{\left[\frac{1}{Z_D(\beta)}\exp(-\beta E_D)\right]\left[\frac{1}{Z_W\alpha}esp(-\alpha E_W)\right]}{\frac{1}{Z_F(\alpha,\beta)}\exp(-F(w))}$$

$$\frac{Z_F(\alpha,\beta)}{Z_D(\beta)Z_W(\alpha)}\cdot\frac{\exp(-\beta E_D-\alpha E_W)}{\exp(-F(w))}$$

$$\frac{Z_F(\alpha,\beta)}{Z_D(\beta)Z_W(\alpha)}$$

and $$Z_F(\alpha,\beta)\approx(2\pi)^{\frac{N}{2}}\left(\det\left(\left(H^{MP}\right)^{-1}\right)\right)^{\frac{1}{2}}\exp\left(-F\left(w^{MP}\right)\right)$$

$$Z_D(\beta)=\frac{1}{P(D|W,\beta,M)}\exp(-\beta E_D)$$

$$Z_W(\alpha)=\frac{1}{P(w|\alpha,M)}\exp(-\alpha E_W)$$

where $H=\beta\nabla^2E_D+\alpha\nabla^2E_W$ is the Hessian matrix of the objective function. The Bayesian regularization minimizes the linear combination of squared errors and weights so that the resulting network has good generalization qualities at the end of training.

In an implementation, the signal processor 110 is a set of algorithms for noise removal and biomarker extraction that includes an outlier removal algorithm based on the mean Euclidean distance (MED) method, a denoising algorithm via a signal-subspace approach, a finite impulse response (FIR) notch filter for 60 Hz line noise removal, an FIR bandpass filter for theta and/or gamma oscillation(s) extraction, and a power extraction algorithm using the Hilbert transform. In an implementation, the signal processor 110 is operable to denoise the electrical signals recorded by the NSP 104 prior to the electrical signals being received by the controller 108. In this implementation, mean Euclidean distance (MED) is computed for each trial with respect to a reference trial. The MED is represented by:

$$MED(i)=\sqrt{\frac{1}{N}\sum_{j=1}^{n}(x_i(j)-x_T(j))^2}$$

where i=1, 2, 3 . . . , n is the trials number, j=1, 2, 3 . . . , N is the sample number of the trial, and $x_T$ is the reference trial. The outliers that exceed a range from the reference trial can be rejected. For instance, trials that exhibit 75% greater than the MED of the reference trial are rejected. However, the disclosure is not limited as such, and any suitable range can be used. The remaining trials can down sampled, such as, for example, to 500 Hz, followed by an anti-aliasing lowpass filtering, such as, for example, at 200 Hz, and further denoised via a subspace approach represented by:

$$B=AQ_SQ_S^T=\left[s_1(t)^T,s_2(t)^T,s_3(t)^T,\ldots,s_m(t)^T\right]^T$$

where $A=[x_1(t)^T, x_2(t)^T, x_3(t)^T, \ldots, x_m(t)^T]^T$ is the matrix of the trials, $Q_s$ is the matrix of the principle eigenvectors decomposed from the sample correlation matrix $\hat{R}=A^TA$, and $s_i$, I=1, 2, 3, . . . , M are the projections of the trials onto the signal subspace.

In an implementation, the signal processor 110 is further operable to extract the biomarkers from the electrical signals recorded by the NSP 104 prior to the electrical signals being received by the controller 108. In an implementation, denoised iEEG signals are bandpass filtered via an FIR filter into theta and/or gamma oscillation(s), and the instantaneous root mean square (RMS) power is extracted from the theta and/or gamma oscillation(s) by applying the Hilbert transform, followed by taking the absolute value.

Figure 5:
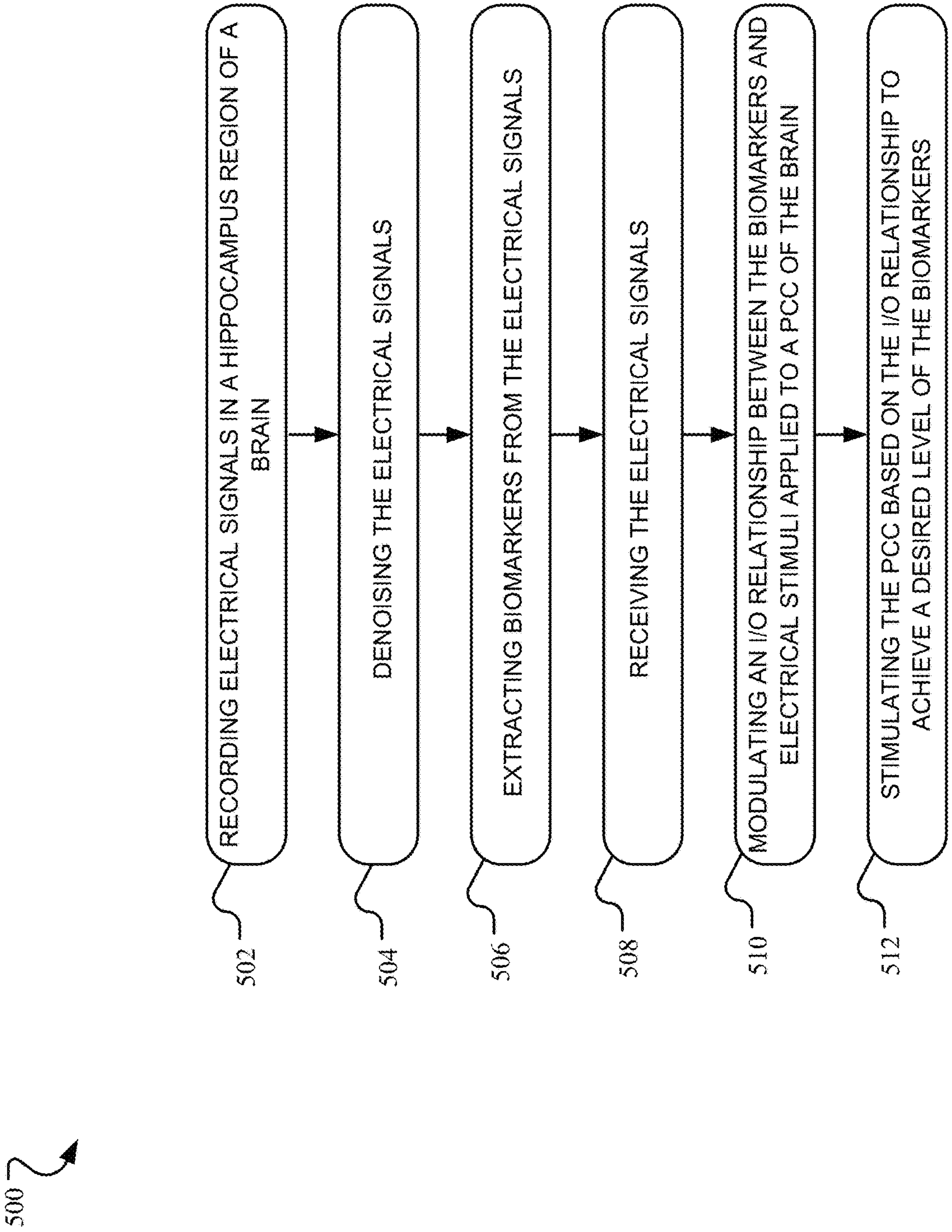
FIG. 5 shows an example flow chart for using the system of FIG. 1 for deep brain stimulation.

Referring to FIG. 5, a method 500 for performing deep brain stimulation via the system 100 is shown. The method 500 is provided by way of example, as there are a variety of ways to carry out the method. The method 500 described herein can be carried out using the configurations and examples illustrated in the figures, for example, and various elements of these figures are referenced in explaining the method 500. Each block shown in FIG. 5 represents one or more processes, methods, or subroutines, carried out in the method 500. Furthermore, the illustrated order of blocks is illustrative only and the order of the blocks can change according to the present disclosure. Additional blocks may be added, or fewer blocks may be utilized, without deviating from the scope of the present disclosure. The method 500 can begin at block 502.

At block 502, electrical signals are recorded via intracranial electrodes disposed in a hippocampus region of a brain using the NSP 104. The electrical signals including biomarkers related to memory encoding, such as, for example, hippocampal theta and gamma oscillatory power. In an embodiment, the electrical signals are acquired using intracranial electroencephalogram (iEEG).

At block 504, the electrical signals including the biomarkers are denoised by the signal processor 110. At block 506, the biomarkers are extracted from the electrical signals by the signal processor 110.

At block 508, the electrical signals are received by the controller 108. At block 510, the controller 108 modulates an input/output (I/O) relationship between the biomarkers and electrical stimuli applied to a posterior cingulate cortex (PCC) of the brain 102. In an implementation, the controller 108 is a proportional integral derivative (PID) controller tuned for the plant 112. In an implementation, the plant 112 is a nonlinear autoregressive with exogenous input neural network (NARXNN). In an implementation, the NARXNN includes a linear autoregressive with exogenous input (ARX) model with nonlinear activation function optimized by a multilayer perceptron (MLP) 114 neural network arranged in a structure having less than three layers, such as, for example a two-layer NARXNN having a hidden layer and an output layer for modeling hippocampal theta and gamma oscillatory power.

At block 512, the controller 108 controls the neurostimulator 106 to stimulate the PCC of the brain 102 based on the I/O relationship to achieve a desired level of the biomarkers.

Figure 7:
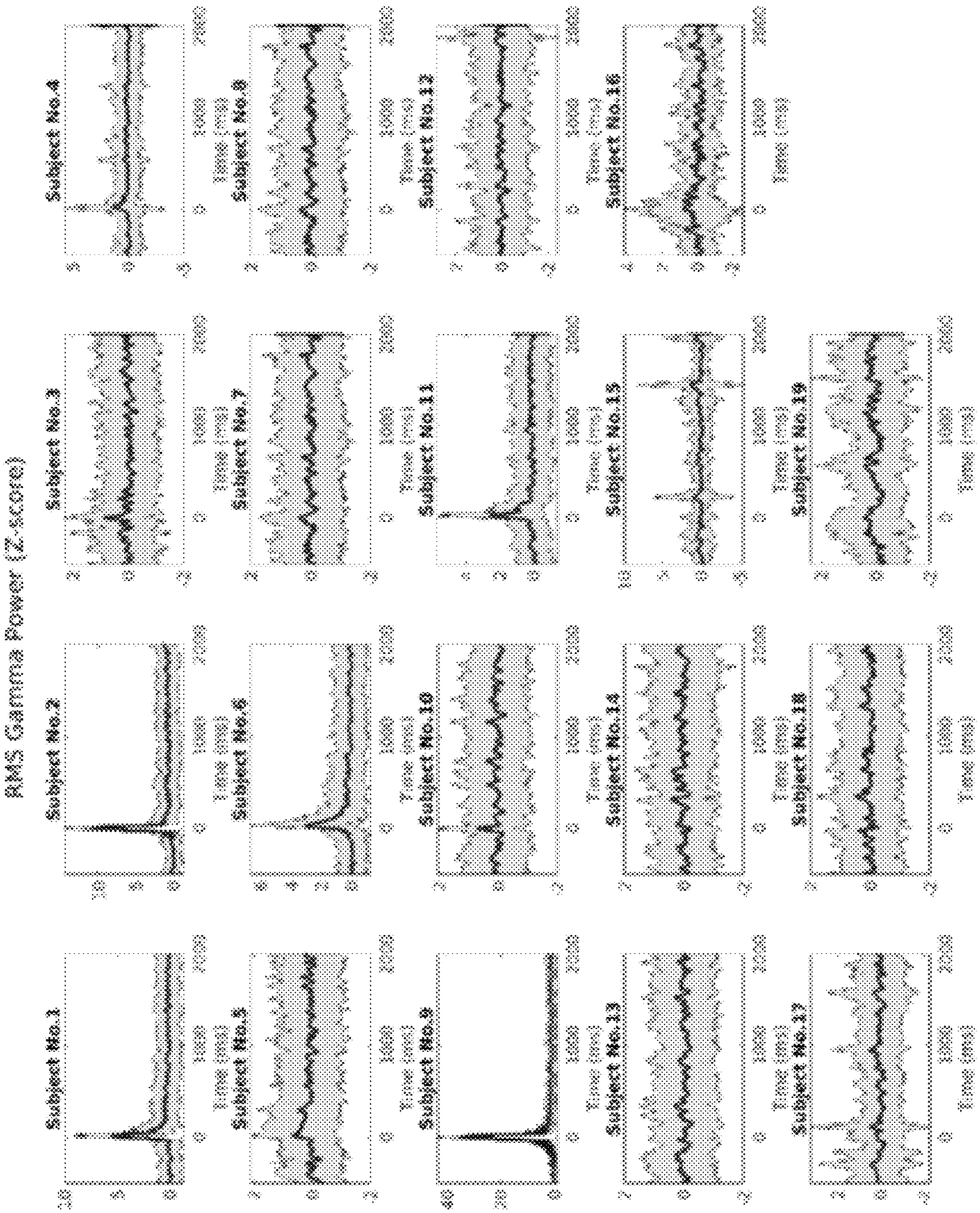
FIG. 7 shows an illustration of RMS gamma power when stimuli were applied to test subjects.
Figure 8:
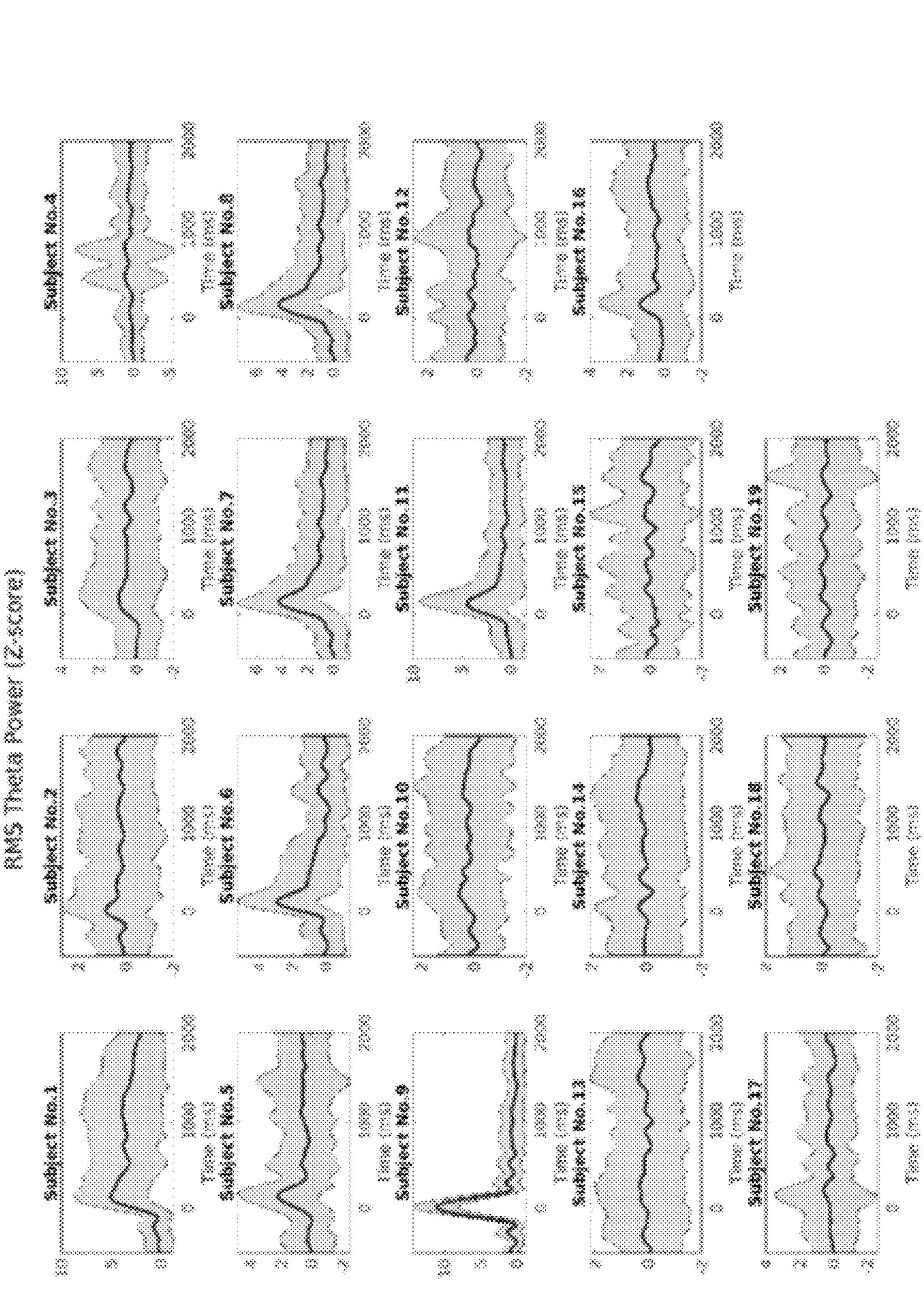
FIG. 8 shows an illustration of RMS theta power when stimuli were applied to test subjects.

Method 500 implemented via system 100 has been found by the inventors to be more effective at modulating theta and gamma hippocampal power to improve episodic memory retention compared to conventional methods. During a study of 19 subjects, dynamical changes of the stimuli-evoked hippocampal oscillatory power in the theta and gamma bands were investigated. In the study, the theta and gamma RMS power trials in a time window of 500 ms before the stimulation (i.e., −500 ms) to 2000 ms after the stimulation (i.e., +2000 ms), where stimuli were onset at 0 ms. Because of the various power levels across different subjects, the power trials were normalized in z-scores by subtracting the mean then dividing by the standard deviation. Increases in the gamma power were observed within 49.36±21.68 ms after stimulation in 15 out of 19 subjects. Similar for the theta power, power increases were observed at an average of 89.15±55.32 ms in 15 of 19 subjects. These results are found in FIGS. 7-8.

Figure 9:
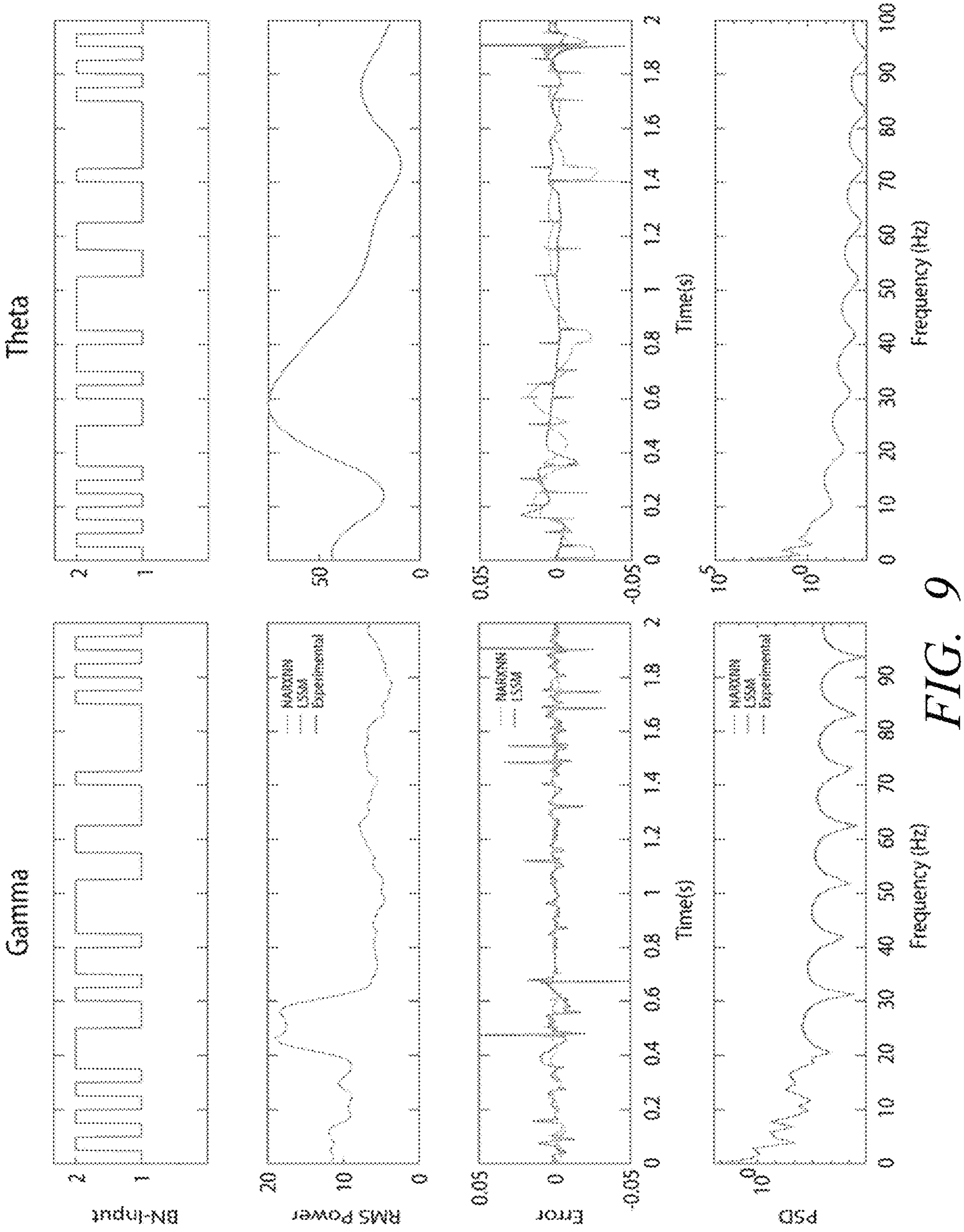
FIG. 9 shows an illustration of overall performance for the system of FIG. 1 using one step ahead prediction where the controller is trained using a NARXNN plant versus a LSSM plant.
Figure 10:
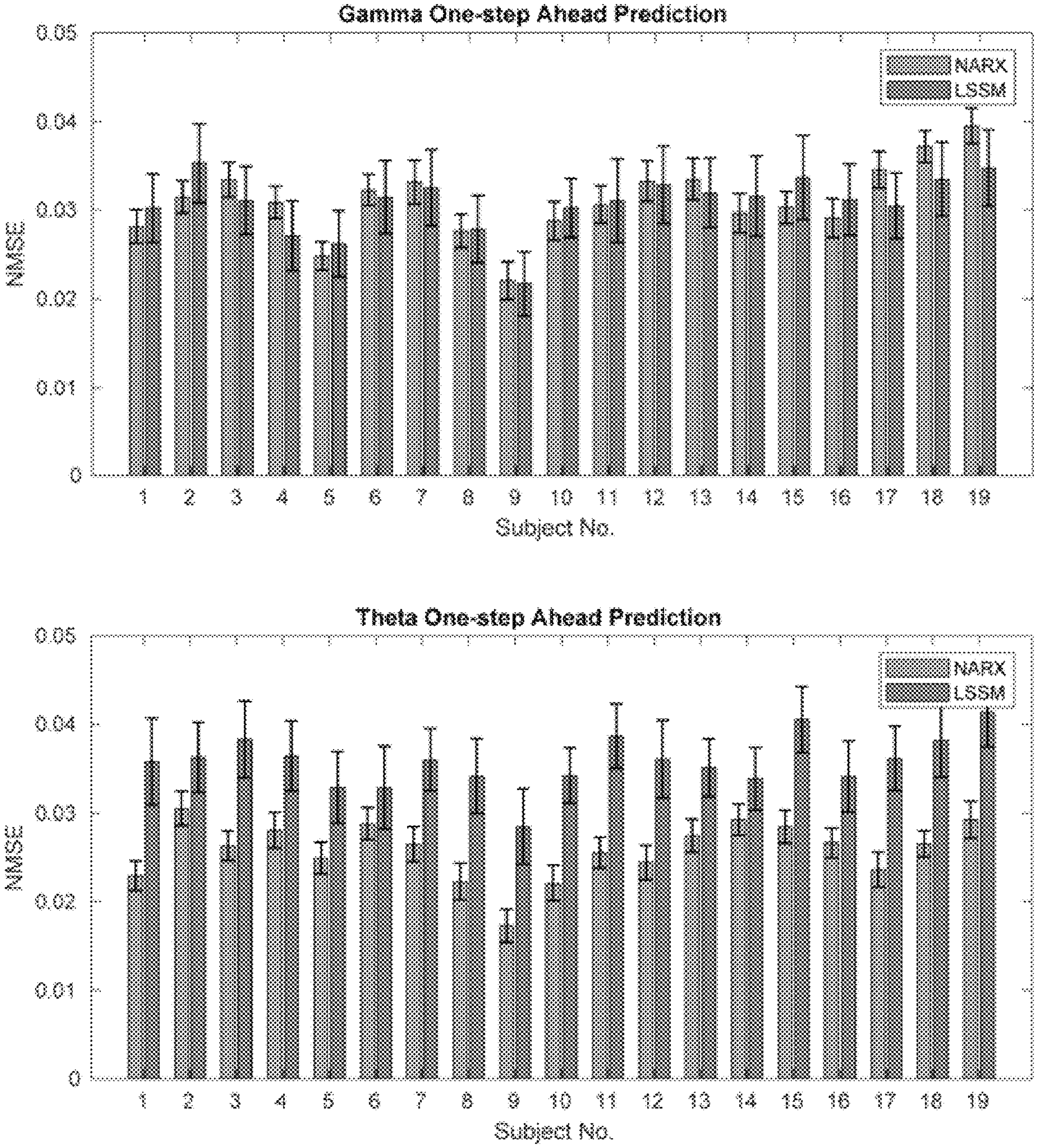
FIG. 10 shows an illustration of averaged normalized mean squared error in one-step-ahead prediction of RMS gamma and theta power for the system of FIG. 1 where the controller is trained using a NARXNN plant versus a LSSM plant.

For the 19 subjects, the NARXNN plant was compared to a LSSM plant. Across 19 subjects, both the NARXNN and LSSM plants accurately predicted the input-driven dynamics of the hippocampal theta and gamma oscillatory activities in response to stimulation. One-step-ahead prediction was performed, where the predictor estimates the next output given the knowledge of current and previous input and output. Both the LSSM and NARXNN plants predicted instantaneous theta and gamma RMS power closely to experimental trials, as expected. FIG. 9 shows an example trace of predicted instantaneous theta and gamma RMS power via LSSM and NARXNN plants, where the prediction error and the power spectral density (PSD) of the predictions versus the experimental data are compared. The overall performance for subject-specific NARXNN versus LSSM in one-step ahead prediction is shown in FIG. 10. Across all subjects, the averaged NMSE of NARXNN predictions was 0.0342±0.007 for the gamma power and 0.0269±0.0010 for the theta power, and the averaged NMSE of LSSM predictions was 0.0322±0.006 for the gamma power and 0.0389±0.008 for theta power.

Figure 11:
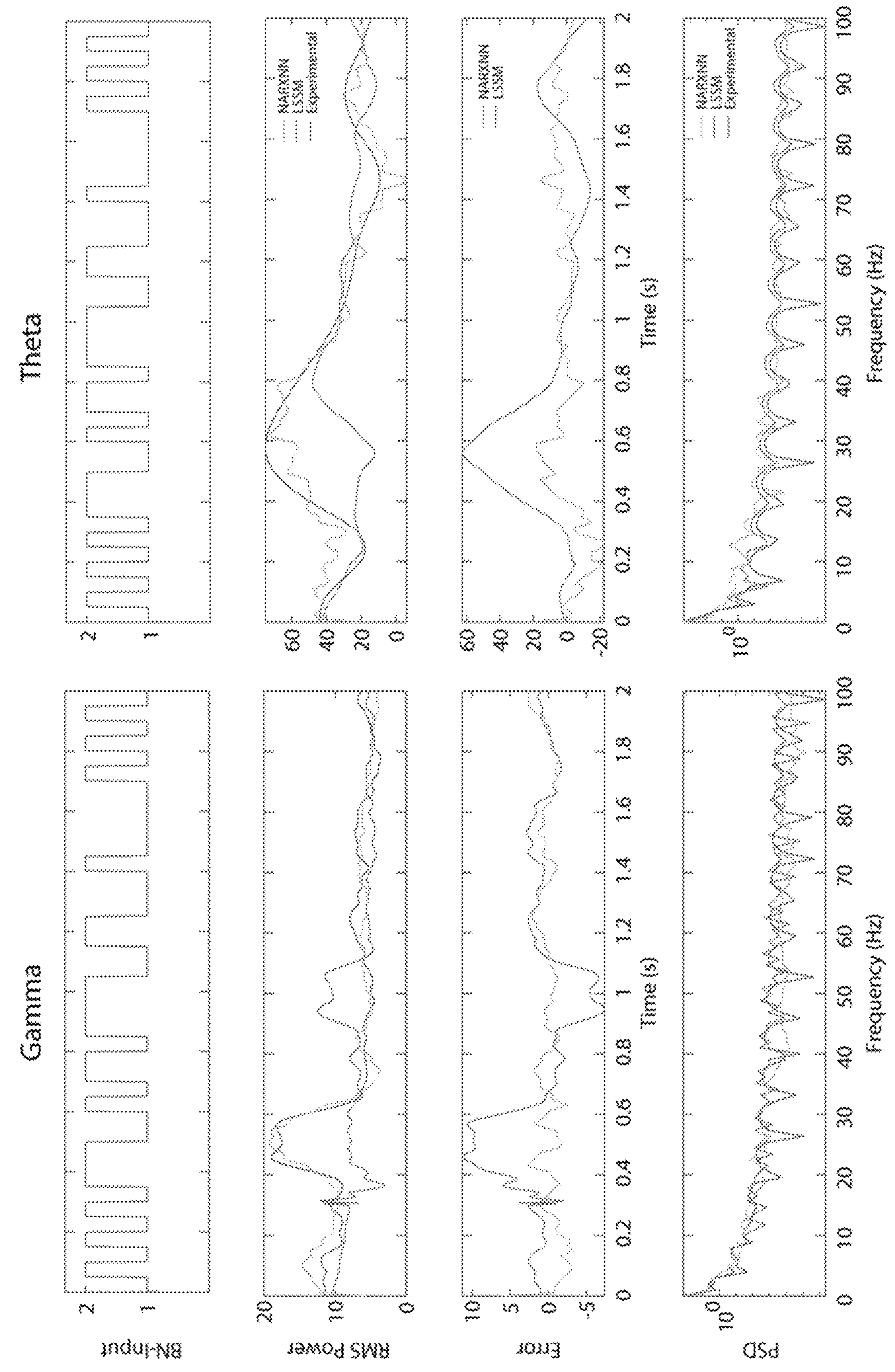
FIG. 11 shows an illustration of a trace of full input driven predicted instantaneous theta and gamma RMS power for the system of FIG. 1 where the controller is trained using a NARXNN plant versus a LSSM plant.
Figure 12:
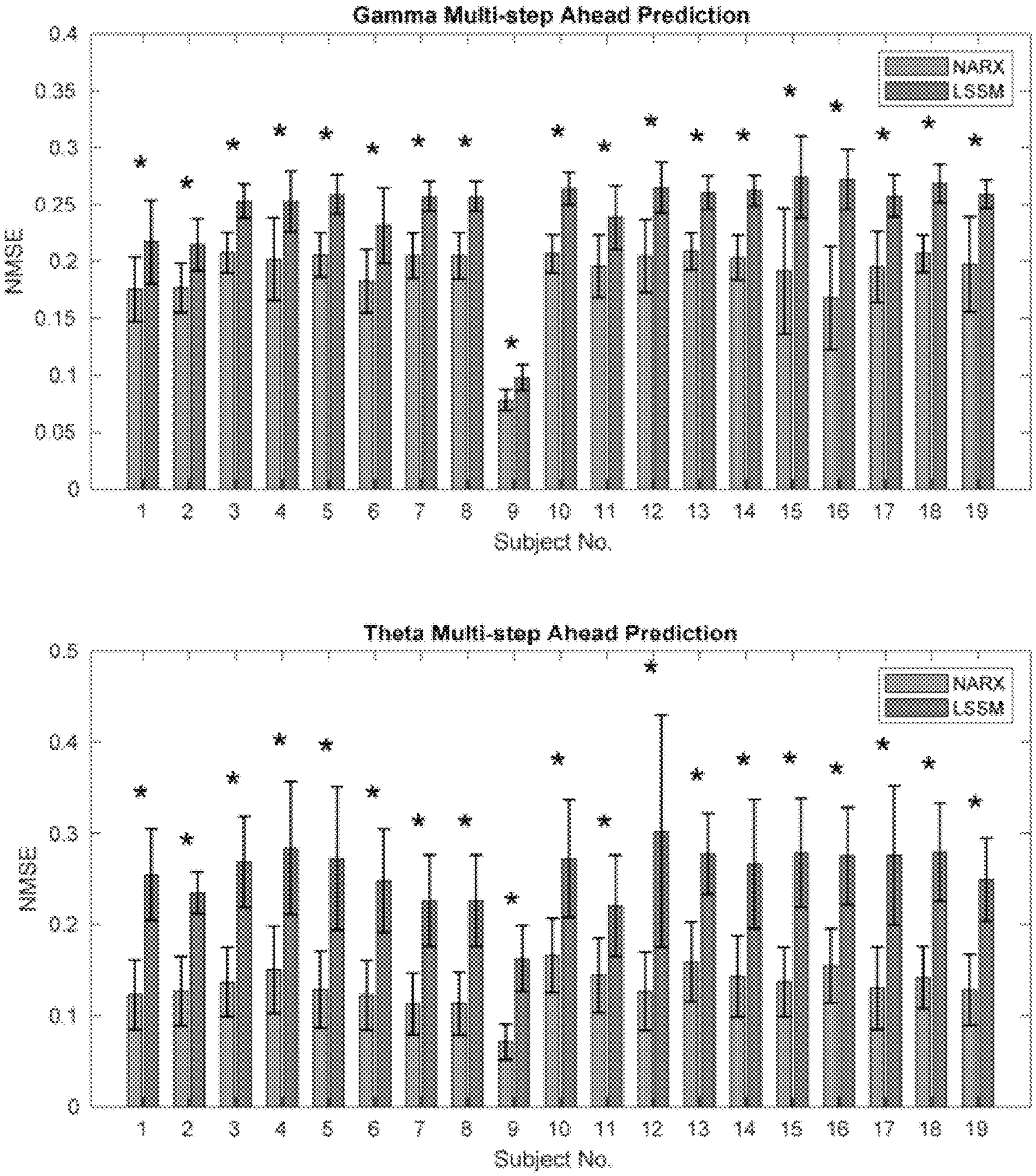
FIG. 12 shows an illustration of averaged normalized mean squared error in full input driven prediction of theta and gamma RMS power for the system of FIG. 1 where the controller is trained using a NARXNN plant versus a LSSM plant.

Full input-driven prediction in both models was implemented. Here, the plants are "simulators" (simulation focused) instead of "predictors" (prediction focused). This input-driven prediction represents how a plant responses to a system input and yields input-driven dynamics of the system. As shown in FIG. 11, the example trace shows that NARXNN introduced some random fluctuation in predicting gamma and theta power but maintained a fair match to the experimental trial, whereas LSSM lost critical temporal resolutions especially within the 0.3-0.8 s time window where theta and gamma exhibited great dynamical changes that LSSM failed to predict accurately. Across all subjects, the averaged NMSE of predictions via NARXNN was 0.179±0.055 for the gamma power and 0.0153±0.071 for the theta, and the averaged NMSE of predictions via LSSM was 0.259±0.082 for the gamma band and 0.288±0.079 for the theta. In all 19 subjects, gamma band power predicted by NARXNN model exhibited less NMSE comparing to the predictions by LSSM model, and they all had significant less NMSE via paired t-tests (p<0.05). For theta power prediction, 19 subjects had less NMSE using NARXNN than using LSSM and all of the subjects were statistically significant (see FIG. 12). Thus, it is shown that the NARXNN plant outperforms the LSSM plant.

Figure 13:
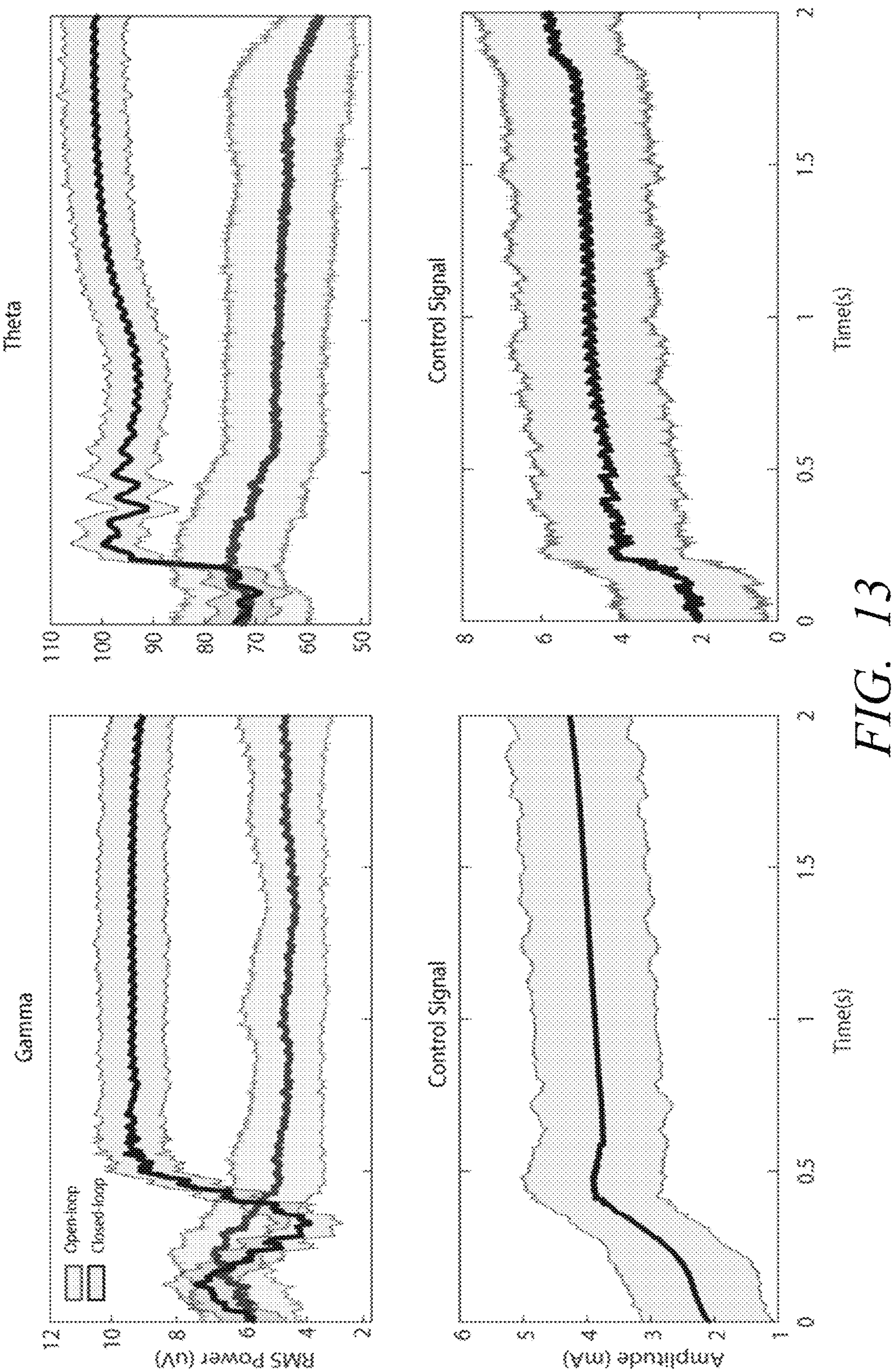
FIG. 13 shows an illustration of power trials from closed-loop versus open-loop control using the system of FIG. 1.
Figure 14:
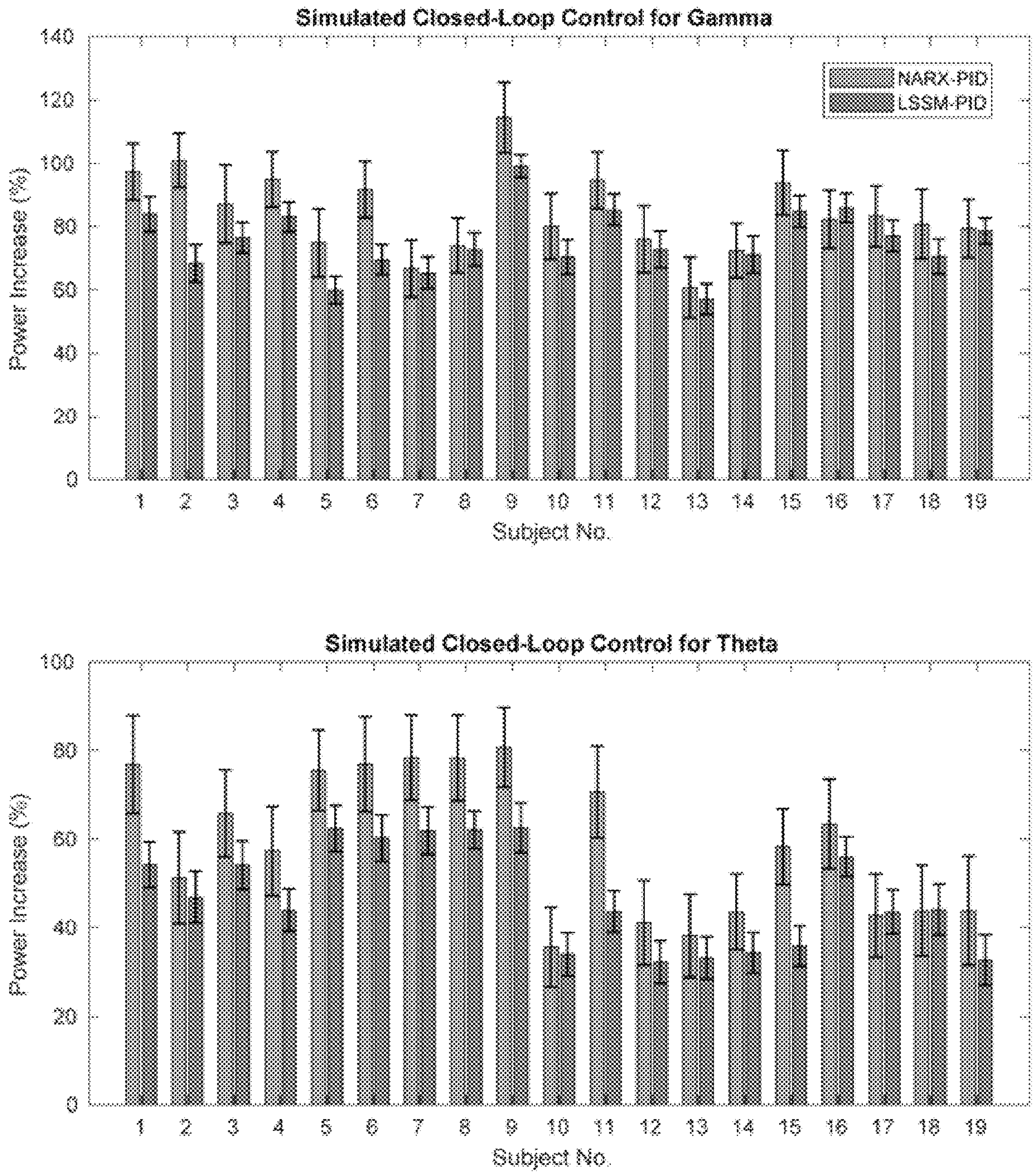
FIG. 14 shown an illustration of power increases in simulated control of hippocampal theta and gamma power using the controller of FIG. 1 trained using a NARXNN plant versus a LSSM plant.

A simulated testbed for the system 100 was created and conducted closed-loop control was conducted using the NARXNN plant, paired with the controller 108 for testing the effectiveness and efficiency in modulating hippocampal theta and gamma power. The controller 108 for each subject-specific NARXNN plant was manually tuned following the Ziegler-Nichols' method, independently. Then, a subject-specific target power level for each theta and gamma oscillations was determined by the highest power level the system 100 was able to achieve while maintaining the control signal (i.e., stimulation amplitude) in a psychological safe range of 0-9 mA. Then, the closed-loop control took place over a course of 2 s, where closed-loop stimulation was onset at t=0, for 76.6±18.8 independent simulations across the 19 subjects. Open-loop stimulation was also simulated using the experimental stimulation input. Example trials of closed-loop control versus open-loop control are found in FIG. 13 where closed-loop control of gamma power was 87.3%±12.6% greater than open-loop power, and closed-loop control of theta power was 56.7%±13.3% greater, using the system 100. This was calculated on averaged theta/gamma power across the entire 2 s of simulation. The averaged time to achieve setpoint using the system 100 was 413.63 ms±211.32 ms for the gamma power and 186.36 ms±59.23 ms for the theta. For comparison, a LSSM-PID closed-loop control architecture was also tested. The LSSM-PID scheme was able to reach a target level, but the control signals were saturated at safety boundary and were not as physiologically realistic as the system 100, which gradually increased the stimulation amplitude to compensate the intrinsic descent hippocampal power to maintain the desired level (see control signals in FIG. 13). By selecting a proper setpoint for each subject, we compared the closed-loop control performance for both the system 100 and LSSM-PID framework. The capability of both systems in modulating and controlling oscillatory power was found and confirmed the superior performance using the architecture of system 100. In 17 of 19 subjects, closed-loop control using the system 100 exhibited greater gamma power increases versus LSSM-PID under the same safety guideline, and 13 of them were statistically significant (p<0.05). The averaged gamma power increase in the closed-loop control using the system 100 was 83.21%±17.62% versus 72.53%±1543.% using the LSSM-PID. For the theta power, we found that 17 out of 19 subjects had greater power increases using the system 100 than LSSM-PID (17 were significant, p<0.05). The averaged theta power increase in closed-loop control, comparing to the experimental power, was 60.05%±15.07% using the system 100 versus 46.67%±9.98% via LSSM-PID. These results are visible in FIG. 14. Thus, the system 100 is superior in modulating oscillatory power compared to the LSSM-PID framework.

Having described several embodiments, it will be recognized by those skilled in the art that various modifications, alternative constructions, and equivalents may be used without departing from the spirit of the present inventive concept. Additionally, a number of well-known processes and elements have not been described in order to avoid unnecessarily obscuring the present inventive concept. Accordingly, this description should not be taken as limiting the scope of the present inventive concept.

Those skilled in the art will appreciate that the presently disclosed embodiments teach by way of example and not by limitation. Therefore, the matter contained in this description or shown in the accompanying drawings should be interpreted as illustrative and not in a limiting sense. The following claims are intended to cover all generic and specific features described herein, as well as all statements of the scope of the method and assemblies, which, as a matter of language, might be said to fall therebetween.

What is claimed is:

1. A system for deep brain stimulation, the system comprising:

intracranial electrodes operable to be disposed in a hippocampus region of a brain and configured to record electrical signals;

a signal processor configured to denoise the electrical signals and process the electrical signals to extract biomarkers from the electrical signals, the biomarkers related to memory encoding;

a neurostimulator configured to stimulate a posterior cingulate cortex (PCC) of the brain; and a controller configured to receive the biomarkers and modulate an input/output (I/O) relationship between the biomarkers and electrical stimuli applied to the (PCC) of the brain by controlling the neurostimulator to stimulate the PCC based on the I/O relationship to achieve a desired level of the biomarkers.

2. The system of claim 1, wherein the electrical signals are acquired using intracranial electroencephalogram (iEEG).

3. The system of claim 1, wherein the biomarkers include hippocampal theta and gamma oscillatory power.

4. The system of claim 1, wherein the intracranial electrodes record the electrical signals using a neural signal processor (NSP).

5. The system of claim 1, wherein the controller is a proportional integral derivative (PID) controller.

6. The system of claim 5, wherein the PID controller is tuned for a plant.

7. The system of claim 6, wherein the plant is a nonlinear autoregressive with exogenous input neural network (NARXNN).

8. The system of claim 7, wherein the NARXNN includes a linear autoregressive with exogenous input (ARX) model with nonlinear activation function optimized by a multilayer perceptron (MLP) neural network arranged in a structure having less than three layers.

9. The system of claim 7, wherein the NARXNN is a two-layer NARXNN having a hidden layer and an output layer for modeling hippocampal theta and gamma oscillatory power.

10. A method for deep brain stimulation, the method comprising:

recording electrical signals via intracranial electrodes disposed in a hippocampus region of a brain;

denoising, via a signal processor, the electrical signals;

processing, via the signal processor, the electrical signals to extract biomarkers from the electrical signals, the biomarkers related to memory encoding;

receiving, via a controller tuned for a plant, the biomarkers; and modulating, via the plant and the controller, an input/output (I/O) relationship between the biomarkers and electrical stimuli applied to a posterior cingulate cortex (PCC) of the brain by controlling a neurostimulator to stimulate the PCC to achieve a desired level of the biomarkers.

11. The method of claim 10, wherein the electrical signals are acquired using intracranial electroencephalogram (iEEG).

12. The method of claim 10, wherein the biomarkers include hippocampal theta and gamma oscillatory power.

13. The method of claim 10, wherein the recording is performed using a neural signal processor (NSP).

14. The method of claim 10, wherein the controller is a proportional integral derivative (PID) controller.

15. The method of claim 14, wherein the plant is a nonlinear autoregressive with exogenous input neural network (NARXNN).

16. The method of claim 15, wherein the NARXNN includes a linear autoregressive with exogenous input (ARX) model with nonlinear activation function optimized by a multilayer perceptron (MLP) neural network arranged in a structure having less than three layers.

17. The method of claim 15, wherein the NARXNN is a two-layer NARXNN having a hidden layer and an output layer for modeling hippocampal theta and gamma oscillatory power.

* * * * *